(12) United States Patent
Bhai

(10) Patent No.: US 8,745,788 B2
(45) Date of Patent: Jun. 10, 2014

(54) SYSTEM AND METHOD FOR CONTROLLING AN AIR MATTRESS

(75) Inventor: Aziz A. Bhai, Batesville, IN (US)

(73) Assignee: Hill-Rom Services. Inc., Batesville, IN (US)

( * ) Notice: Subject to any disclaimer, the term of this patent is extended or adjusted under 35 U.S.C. 154(b) by 937 days.

(21) Appl. No.: 11/996,696

(22) PCT Filed: Jul. 25, 2006

(86) PCT No.: PCT/US2006/028729
§ 371 (c)(1),
(2), (4) Date: Jan. 24, 2008

(87) PCT Pub. No.: WO2007/016054
PCT Pub. Date: Feb. 8, 2007

(65) Prior Publication Data
US 2008/0189865 A1    Aug. 14, 2008

Related U.S. Application Data

(60) Provisional application No. 60/702,645, filed on Jul. 26, 2005.

(51) Int. Cl.
*A61G 7/00* (2006.01)

(52) U.S. Cl.
USPC ........................................ 5/600; 5/617; 5/713

(58) Field of Classification Search
USPC ..................... 5/600, 613, 706, 710, 713, 617
See application file for complete search history.

(56) References Cited

U.S. PATENT DOCUMENTS

| | | | |
|---|---|---|---|
| 779,576 A | 1/1905 | Berryman |
| 1,772,310 A | 8/1930 | Hart |
| 3,303,518 A | 2/1967 | Ingram |
| 3,462,778 A | 8/1969 | Whitney |
| 3,674,019 A | 7/1972 | Grant |
| 3,678,520 A | 7/1972 | Evans |
| 3,772,717 A | 11/1973 | Yuen et al. |
| 3,879,776 A | 4/1975 | Solen |
| 3,882,425 A | 5/1975 | Briley |
| 3,978,530 A | 9/1976 | Amarantos |
| 4,015,928 A | 4/1977 | Carlson |

(Continued)

FOREIGN PATENT DOCUMENTS

| CA | 2 393 880 | 1/2004 |
|---|---|---|
| DE | 103 16 162 A1 | 10/2004 |

(Continued)

OTHER PUBLICATIONS

Renaissance™, Therapeutic Mattress Replacement System, Pegausus Airwave Inc., date unknown.

(Continued)

*Primary Examiner* — Nicholas Polito
(74) *Attorney, Agent, or Firm* — Barnes & Thornburg LLP

(57) ABSTRACT

A patient support (10, 14) includes a source of pressurized air (64), a bladder (30), a valve (66) in fluid communication with the source of pressurized air (64) and to the bladder (30), a pressure sensor (28) in fluid communication with the bladder (30), and a controller (26) responsive to a pressure signal from the pressure sensor (28). The controller (26) may determine a rate of change of pressure within the bladder (30) and may store historical pressure data.

20 Claims, 12 Drawing Sheets

(56) References Cited

U.S. PATENT DOCUMENTS

| | | |
|---|---|---|
| 4,042,988 A | 8/1977 | Holliday |
| 4,120,278 A | 10/1978 | Ward |
| 4,150,654 A | 4/1979 | Heitzman et al. |
| 4,193,149 A | 3/1980 | Welch |
| 4,220,312 A | 9/1980 | Pauliukonis |
| 4,225,989 A | 10/1980 | Corbett et al. |
| 4,267,611 A | 5/1981 | Agulnick |
| 4,336,621 A | 6/1982 | Schwartz et al. |
| 4,391,009 A | 7/1983 | Schild et al. |
| 4,472,847 A | 9/1984 | Gammons et al. |
| 4,477,935 A | 10/1984 | Griffin |
| 4,483,029 A | 11/1984 | Paul |
| 4,525,885 A | 7/1985 | Hunt et al. |
| 4,527,298 A | 7/1985 | Moulton |
| 4,527,715 A | 7/1985 | Rosenbaum |
| 4,541,135 A | 9/1985 | Karpov |
| 4,637,083 A | 1/1987 | Goodwin |
| 4,638,519 A | 1/1987 | Hess |
| 4,639,960 A | 2/1987 | Guillen et al. |
| 4,679,264 A | 7/1987 | Mollura |
| 4,685,163 A | 8/1987 | Guillen et al. |
| 4,803,744 A | 2/1989 | Peck et al. |
| 4,807,313 A | 2/1989 | Ryder et al. |
| 4,825,486 A | 5/1989 | Kimura et al. |
| 4,833,461 A | 5/1989 | Yeager |
| 4,839,512 A | 6/1989 | Speck |
| 4,904,830 A | 2/1990 | Rizzuto |
| 4,934,468 A | 6/1990 | Koerber, Sr. et al. |
| 4,940,861 A | 7/1990 | Rizzuto |
| 4,944,060 A | 7/1990 | Peery et al. |
| 4,951,335 A | 8/1990 | Eady |
| 4,953,244 A | 9/1990 | Koerber, Sr. et al. |
| 4,953,247 A | 9/1990 | Hasty |
| 4,993,920 A | 2/1991 | Harkleroad et al. |
| 4,995,124 A * | 2/1991 | Wridge et al. ............... 5/709 |
| 5,020,176 A | 6/1991 | Dotson |
| 5,029,352 A | 7/1991 | Hargest et al. |
| 5,036,559 A | 8/1991 | Hargest |
| 5,060,174 A | 10/1991 | Gross |
| 5,067,189 A | 11/1991 | Weedling et al. |
| 5,117,518 A | 6/1992 | Schild |
| 5,121,512 A | 6/1992 | Kaufmann |
| 5,129,115 A | 7/1992 | Higgins et al. |
| 5,140,309 A | 8/1992 | Gusakov |
| 5,163,196 A | 11/1992 | Graebe et al. |
| 5,168,589 A | 12/1992 | Stroh et al. |
| 5,170,364 A * | 12/1992 | Gross et al. ............... 702/139 |
| 5,179,920 A | 1/1993 | Bender |
| 5,183,518 A | 2/1993 | Radon |
| 5,184,122 A | 2/1993 | Decious et al. |
| 5,189,742 A | 3/1993 | Schild |
| 5,243,723 A | 9/1993 | Cotner et al. |
| 5,249,318 A | 10/1993 | Loadsman |
| 5,251,349 A | 10/1993 | Thomas et al. |
| 5,269,030 A | 12/1993 | Pahno et al. |
| 5,276,432 A | 1/1994 | Travis |
| 5,325,551 A | 7/1994 | Tappel et al. |
| 5,364,162 A | 11/1994 | Bar et al. |
| 5,394,577 A | 3/1995 | James et al. |
| 5,396,671 A | 3/1995 | Stacy |
| 5,421,044 A | 6/1995 | Steensen |
| 5,483,709 A | 1/1996 | Foster et al. |
| 5,483,711 A | 1/1996 | Hargest et al. |
| 5,539,942 A | 7/1996 | Melou |
| 5,561,873 A | 10/1996 | Weedling |
| 5,561,875 A | 10/1996 | Graebe |
| 5,564,142 A | 10/1996 | Liu |
| 5,586,346 A | 12/1996 | Stacy et al. |
| 5,596,781 A | 1/1997 | Graebe |
| 5,611,096 A | 3/1997 | Bartlett et al. |
| 5,611,772 A | 3/1997 | Fujimoto et al. |
| 5,619,764 A | 4/1997 | Lopau |
| 5,623,736 A | 4/1997 | Soltani et al. |
| 5,634,224 A | 6/1997 | Gates |
| 5,634,225 A | 6/1997 | Miller, Sr. et al. |
| 5,651,153 A | 7/1997 | Goodrich |
| 5,680,036 A | 10/1997 | Faulk |
| D386,035 S | 11/1997 | Matsler et al. |
| 5,684,460 A | 11/1997 | Scanlon |
| 5,689,845 A | 11/1997 | Sobieralski |
| 5,699,570 A | 12/1997 | Wilkinson et al. |
| 5,701,622 A | 12/1997 | Biggie et al. |
| 5,745,942 A | 5/1998 | Wilkerson |
| 5,765,246 A | 6/1998 | Shoenhair |
| 5,774,917 A | 7/1998 | Liu |
| 5,787,531 A | 8/1998 | Pepe |
| 5,794,288 A | 8/1998 | Soltani et al. |
| 5,806,572 A | 9/1998 | Voller |
| 5,815,864 A | 10/1998 | Sloop |
| 5,815,865 A | 10/1998 | Washburn et al. |
| 5,829,081 A | 11/1998 | Pearce |
| 5,845,352 A | 12/1998 | Matsler et al. |
| 5,873,137 A * | 2/1999 | Yavets-Chen ............... 5/713 |
| D407,353 S | 3/1999 | Bar et al. |
| D408,767 S | 4/1999 | Bar et al. |
| 5,890,245 A | 4/1999 | Klearman et al. |
| 5,917,180 A | 6/1999 | Reimer et al. |
| D412,685 S | 8/1999 | Bar et al. |
| D413,085 S | 8/1999 | Bar et al. |
| D413,841 S | 9/1999 | Bar et al. |
| 5,954,402 A | 9/1999 | McInturff |
| D415,567 S | 10/1999 | Bar |
| D415,834 S | 10/1999 | Bar |
| 5,970,789 A | 10/1999 | Meyer et al. |
| D416,326 S | 11/1999 | Bar |
| 5,984,418 A | 11/1999 | McInturff |
| 6,009,580 A | 1/2000 | Caminade et al. |
| 6,014,346 A | 1/2000 | Malone |
| 6,021,800 A | 2/2000 | Schild et al. |
| 6,058,538 A | 5/2000 | Chapman et al. |
| 6,094,762 A | 8/2000 | Viard et al. |
| 6,095,611 A | 8/2000 | Bar et al. |
| 6,098,222 A | 8/2000 | Hand et al. |
| 6,134,732 A | 10/2000 | Chapman et al. |
| 6,145,142 A | 11/2000 | Rechin et al. |
| 6,148,461 A | 11/2000 | Cook et al. |
| 6,165,142 A | 12/2000 | Bar |
| D439,098 S | 3/2001 | Matsler et al. |
| 6,212,718 B1 | 4/2001 | Stolpmann et al. |
| D446,674 S | 8/2001 | Chapman et al. |
| 6,280,392 B1 | 8/2001 | Yoshimi et al. |
| 6,349,439 B1 | 2/2002 | Cook et al. |
| 6,353,950 B1 * | 3/2002 | Bartlett et al. ............... 5/617 |
| 6,385,804 B1 | 5/2002 | Barber et al. |
| 6,412,129 B1 | 7/2002 | Wu |
| D463,701 S | 10/2002 | Borcherding et al. |
| 6,474,743 B1 | 11/2002 | Harker et al. |
| 6,487,739 B1 | 12/2002 | Harker |
| 6,560,804 B2 | 5/2003 | Wise et al. |
| 6,564,410 B2 | 5/2003 | Graebe et al. |
| 6,593,588 B1 | 7/2003 | Reimer |
| 6,623,080 B2 | 9/2003 | Clapper |
| 6,646,556 B1 | 11/2003 | Smith et al. |
| 6,686,711 B2 | 2/2004 | Rose et al. |
| 6,687,936 B2 | 2/2004 | Graebe et al. |
| 6,687,937 B2 | 2/2004 | Harker |
| 6,701,556 B2 | 3/2004 | Romano et al. |
| 6,701,558 B2 | 3/2004 | VanSteenburg |
| 6,721,980 B1 * | 4/2004 | Price et al. ............... 5/713 |
| 6,848,135 B1 | 2/2005 | Kohlman |
| 6,877,178 B2 | 4/2005 | Chapman et al. |
| 6,892,405 B1 | 5/2005 | Dimitriu et al. |
| 6,987,232 B2 | 1/2006 | Smith et al. |
| 7,145,461 B2 * | 12/2006 | Lehrman et al. ............ 340/573.1 |
| 2001/0011480 A1 | 8/2001 | Reimer |
| 2002/0066143 A1 | 6/2002 | Graebe et al. |
| 2003/0030319 A1 | 2/2003 | Clapper |
| 2005/0172398 A1 | 8/2005 | Smith et al. |
| 2006/0152378 A1 | 7/2006 | Lokhorst et al. |

FOREIGN PATENT DOCUMENTS

| | | |
|---|---|---|
| DE | 103 33 742 A1 | 2/2005 |
| EP | 0 560 563 A1 | 9/1993 |

(56) References Cited

FOREIGN PATENT DOCUMENTS

| | | |
|---|---|---|
| EP | 0 853 918 A2 | 7/1998 |
| EP | 1 271 441 A2 | 1/2003 |
| FR | 2 757 377 | 6/1998 |
| FR | 2 814 062 | 3/2002 |
| GB | 159299 | 2/1921 |
| GB | 959103 | 5/1964 |
| GB | 2 090 734 | 7/1982 |
| GB | 2 092 439 A | 8/1982 |
| GB | 2 167 293 A | 5/1986 |
| GB | 2 197 192 A | 5/1988 |
| GB | 2 199 803 A | 7/1988 |
| GB | 2 267 217 A | 12/1993 |
| GB | 2 307 402 A | 5/1997 |
| WO | WO 94/09686 | 5/1984 |
| WO | WO 86/02244 | 4/1986 |
| WO | WO 86/05973 | 10/1986 |
| WO | WO 95/31920 | 11/1995 |
| WO | WO 96/33641 | 10/1996 |
| WO | WO 97/17869 | 5/1997 |
| WO | WO 98/24345 | 6/1998 |
| WO | WO 99/39613 | 8/1999 |
| WO | WO 01/09695 A1 | 2/2001 |
| WO | WO 01/74287 A1 | 10/2001 |
| WO | WO 02/45641 A1 | 6/2002 |
| WO | WO 2004/006768 | 1/2004 |
| WO | WO 2005/013878 | 2/2005 |

OTHER PUBLICATIONS

A Hill-Rom solution, ACUCAIRE Continuous Airflow System, date unknown.
Air Flow 500 Mattress Replacement System, Atlantis Medical, Milltown, NJ, date unknown.
Apropos, CRS-8500, National Patient Care Systems, date unknown.
ASAP II Therapy System, DynaMedics Corporation, London, ON, Canada, Mar. 1995.
Bazooka, Innovative Medical System, Manchester, NH, 1995.
DFS® Homecare Advanced Dynamic Flotation System, HNE Healthcare, Manalapan, NJ, date unknown.
Economic Relief, Bio Therapy® Plus, Sunrise Medical Bio Clinic, Ontario, CA, date unknown.
First Step, Mattress Replacement System, KCI, San Antonio, TX, 1991.
Gaymar Sof-Care Plus © CompanionO System, Gaymar Industries, Inc., 1994.
Hill-Rom PrimeAire ARS Pressure Relief Mattress, date unknown.
Impression, Pressure Relief Therapy, KCI, date unknown.
LUMEX AkroTech 4000, Lumex, date unknown.
microAIRO 1000, GSI Medical Systems, Carmel, NY, 1989.
PRO 2000 MRS, Pneu-Care Series, Cardio Systems, Dallas, TX, date unknown.
Prodigy Mattress Crown Theraputics, Inc., date unknown.
Roho Dry Flotation Isolette see roho.com/medical/isolette.jsp, date unknown.
ROHO series Crown Therapautic, Inc. See woundheal.com, date unknown.
Tytex Group AirX #D Spacer Fabric see tytex.cms.digitalis.dk, date unknown.
International Search Report and Written Opinion for PCT/US06/28729, dated Jul. 21, 2008.
Supplemental European Search Report for 06 81 3228.1, dated Apr. 4, 2014, 10 pages.

* cited by examiner

SYSTEM AND METHOD FOR CONTROLLING AN AIR MATTRESS

RELATED APPLICATIONS

This application is the U.S. national phase of PCT/US2006/028729 filed Jul. 25, 2006. PCT/US2006/028729 claims priority to U.S. Provisional Patent Application No. 60/702,645 filed Jul. 26, 2005. The entire disclosures of both of PCT/US2006/028729 and U.S. Ser. No. 60/702,645 are hereby incorporated by reference.

BACKGROUND OF THE INVENTION

The present disclosure relates to a control system for the control of pressure in a patient support. More particularly, the present disclosure relates to a control system for an inflatable support surface that utilizes pressure data to determine a patient's position on the patient support.

Patient supports, such as hospital beds, and some beds used at home have inflatable support surfaces such as mattresses, for example, on which a person is supported. Such mattresses have one or more air bladders which are inflated and deflated to control the pressure in the bladders. The pressure in the bladders correlates to the interface pressure between the skin of the person supported on the surface and the support surface. Prolonged exposure to excessive pressure and/or skin shear tends to break down the skin and form pressure ulcers, also known as bed sores.

SUMMARY OF THE INVENTION

The present disclosure comprises one or more of the features recited in the appended claims and/or the following features which, alone or in any combination, may comprise patentable subject matter:

According to this disclosure, a patient support may comprise a source of pressurized air, a valve, a bladder, a pressure sensor and a controller. The valve may be in fluid communication with the source of pressurized air and with the bladder. The bladder may be in fluid communication with the pressure sensor. The controller may be in electrical communication with the source of pressurized air, the valve, and the first pressure sensor. The controller may comprise a processor, and a memory device electrically coupled to the processor. The memory device may store a plurality of instructions which, when executed by the processor, cause the processor to operate the source of pressurized air and the valve to inflate the bladder, monitor the first pressure signal during the inflation to determine a rate of change of pressure in the bladder, and determine whether the patient is supported on the bladder based on the rate of change. The bladder may be inflated or deflated and the rate of change of pressure may be determined during inflation or deflation as the case may be. The patient support may have multiple bladders and the rate of change of pressure may be determined for one or more of the multiple bladders.

The processor may operate the valve to deflate the first bladder, monitor the first pressure signal during the deflation to determine a rate of change of pressure in the first bladder, and determine whether the patient is supported on the first bladder.

The processor may establish a target pressure for the first bladder, inflate the first bladder to a pressure within an acceptable tolerance of the target pressure, monitor the first pressure signal, compare the first pressure signal to the target pressure to determine a deviation of the first pressure signal from the target pressure, accumulate the magnitude of pressure deviation over time, and output a signal if the accumulated magnitude exceeds a maximum value. The system may inflate or deflate the bladder back to within the tolerance range in response to the signal. The processor, therefore, may allow a period of time to elapse when the pressure is outside of the tolerance range before pressure adjustments are made. The period of elapsed time may vary depending on how far outside of the tolerance the measured pressure deviates.

The patient support may comprise the source of pressurized air; the first bladder and a second bladder; the first valve and second, third and fourth valves; the first pressure sensor and a second pressure sensor; and the controller. The first valve may be in fluid communication with the source of pressurized air and with the first bladder and configured to control the flow of air between the source of pressurized air and the first bladder. The second valve may be in fluid communication with the first bladder and configured to control the flow of air out of the first bladder. The third valve may be in fluid communication with the source of pressurized air and with the second bladder and configured to control the flow of air between the source of pressurized air and the second bladder. The fourth valve may be in fluid communication with the second bladder and configured to control the flow of air out of the second bladder. The first pressure sensor may be in fluid communication with the first bladder and produce a first pressure signal indicative of air pressure within the first bladder. The second pressure sensor may be in fluid communication with the second bladder and produce a second pressure signal indicative of air pressure within the second bladder. The controller may be in electrical communication with the source of pressurized air, valves, and pressure sensors. The processor may establish a position of the patient supported on the first bladder by comparing the rate of change of pressure in the first bladder to the rate of change of pressure in the second bladder, monitor the first and second pressure signals, and determine whether the patient has changed positions on the first and second bladders.

The processor may cause the processor to establish a target pressure for the first bladder, determine the acceptable tolerance for the target pressure by evaluating the stability of the first pressure signal over time, and control pressure in the first bladder to within an acceptable tolerance of the target pressure by operating the source of pressurized air and the first valve to inflate the first bladder and operate the second valve to deflate the first bladder and monitor the first pressure signal during the operation of the source of pressurized air and first and second valves.

The control system may be operable to control a pressure at which the at least one bladder is inflated, the pressure being determined automatically as a function of a weight of the patient, a position of the patient on the patient support, and an amount that a least a portion of the patient support is articulated, wherein the position of the person is automatically determined by the control system by monitoring a rate of change of pressure in the at least one inflatable bladder.

The controller may determine that the patient has changed positions by moving between a supine position and a side-lying position. The controller may determine that the patient has changed positions by moving between a sitting up position and a supine position. The controller may determine that the patient has changed positions by moving between a prone position and a side-lying position. The controller may determine that the patient has changed positions by moving between a sitting up position and a supine position.

A method of controlling pressure in an inflatable zone of a patient support surface supported on a patient support apparatus may comprise multiple steps. One step may comprise inflating the inflatable zone to a first target pressure. Another step may comprise further inflating the inflatable zone. Yet another step may comprise determining a rate of change of pressure in the inflatable zone resulting from the further inflation of the inflatable zone. Still another step may comprise comparing the rate of change of pressure in the inflatable zone to a threshold value. Yet still another step may comprise adjusting the inflation of the inflatable zone to a second target pressure if the comparison of the pressure rate of change to the threshold value meets predetermined criteria. The predetermined criteria may be a function of the weight of a patient supported on the patient support apparatus or an angle of articulation of a section of the patient support apparatus.

Yet another method of controlling pressure in a first inflatable zone of a patient support surface may comprise multiple steps as well. One step may comprise inflating the first inflatable zone to a first target pressure and inflating a second inflatable zone of the support surface to a second target pressure. Another step may comprise further inflating the second inflatable zone. Yet another step may comprise determining a rate of change of pressure in the second inflatable zone resulting from the further inflation of the second inflatable zone. Still another step may comprise comparing the rate of change of pressure in the second inflatable zone to a threshold value. Yet still another step may comprise adjusting the inflation of the first inflatable zone to a third target pressure if the comparison of the pressure rate of change to the threshold value meets a predetermined criteria. The predetermined criteria may be a function of the weight of a patient supported on the patient support apparatus or an angle of articulation of a section of the patient support apparatus.

The processor of the controller may determine the rate of change of pressure in a bladder by comparing the change from a first pressure to a second pressure over a known time interval. The processor may compare a rate of change to a threshold value to determine if a patient is supported on the bladder. In some embodiments, the determination that a patient is supported on the supported on the bladder may be based on the rate of change being lower than the threshold. In other embodiments, the determination that a patient is supported on the supported on the bladder may be based on the rate of change being higher than the threshold.

The patient support may further include a weight sensor, such as a load beam, in electrical communication with the processor to input a signal indicative of at least a portion of the weight of the patient supported on the patient support. The threshold value or predetermined criteria may be a function of the patient weight The patient support may include a position sensor, such as a potentiometer, in electrical communication with the processor to input a signal indicative of the articulation position of a section of the patient support. The threshold value or predetermined criteria may be a function of the articulation position.

The processor may filter the pressure signal. The processor may filter the signal either during inflation of deflation. The processor may filter the pressure data by taking an average of a number of pressure data points.

In some embodiments, the patient support may further comprise an additional bladder and an additional pressure sensor which communicates with the additional bladder. The controller may be further responsive to the rate of change in the additional bladder and the threshold value or predetermined criteria may be a function of the rate of change in the additional bladder.

In some embodiments, pressure deviations above the target pressure may have a first weighting and pressure deviations below the target pressure may have a second weighting and the potential damage accumulation may include the weighted pressure deviations. In some embodiments, the second weighting factor may be less than the first weighting factor.

The predetermined criteria for damage may be a function of the patient weight. The controller may be responsive to an additional pressure signal from an additional bladder to accumulate the potential damage from the first bladder and the additional bladder and to adjust the target pressure in the bladders if the combined potential damage exceeds a second predetermined value. The second predetermined value may be less than the combined sum of the predetermined values for each of the bladders independently.

The controller may be responsive to the rate of change of pressure within the bladder to determine whether a patient supported on the patient support has transitioned between a lying position and a sitting position. In some embodiments, the bladder which is analyzed to determine whether the patient has sat up may be positioned to support the back of the patient. In other embodiments, the bladder which is analyzed to determine whether the patient has sat up may be positioned to support the buttocks of the patient. In some embodiments, the controller may be responsive to the rate of change of pressure within multiple bladders to determine whether the patient supported on the patient support has transitioned between a lying position and a sitting position.

The controller may perform statistical analysis on the rate of pressure change data in determining if predetermined criteria have been met.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
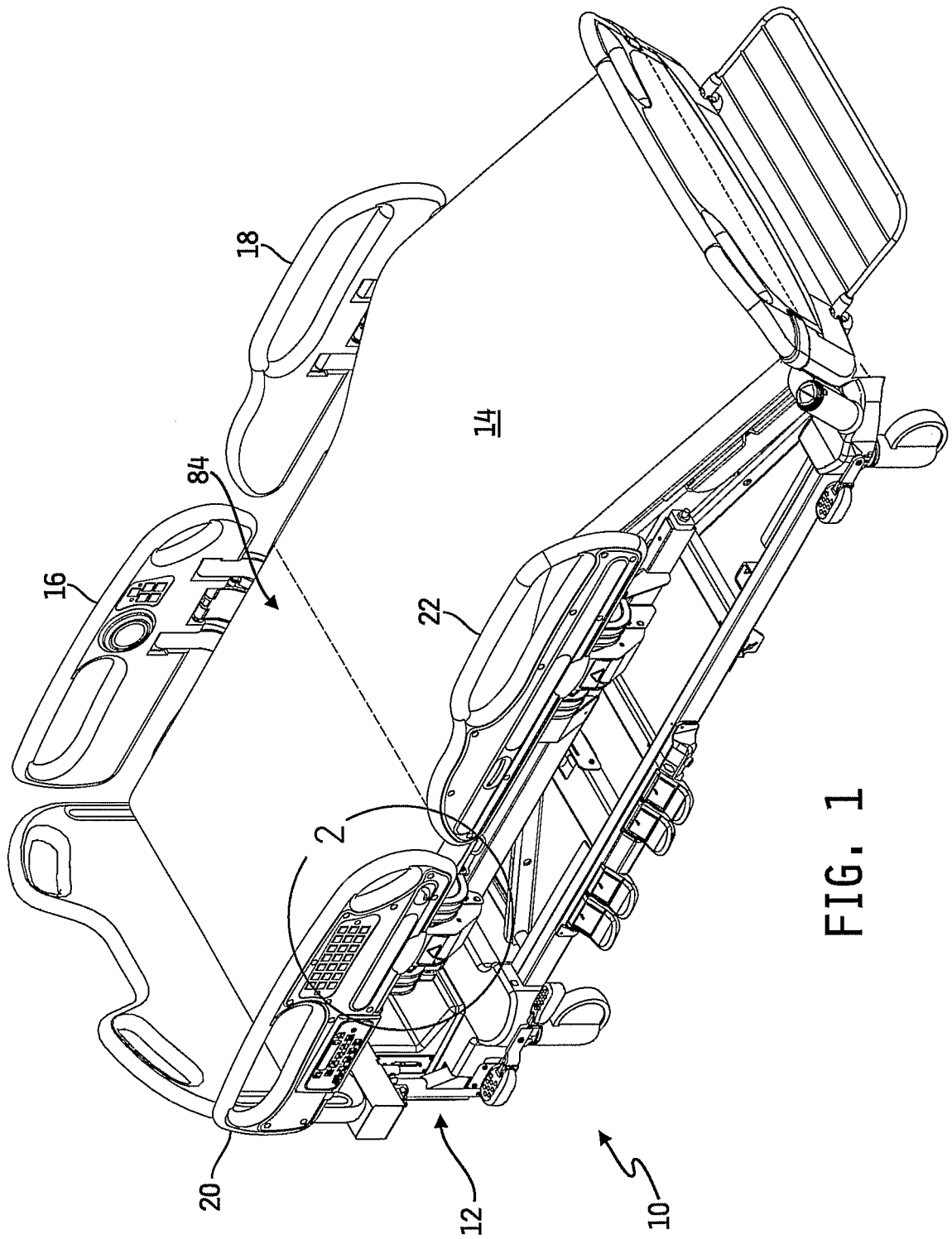
FIG. 1 is a perspective view of a hospital bed employing an embodiment of the control system of the present disclosure, the hospital bed including an articulable frame, siderails, and a mattress.
Figure 3:
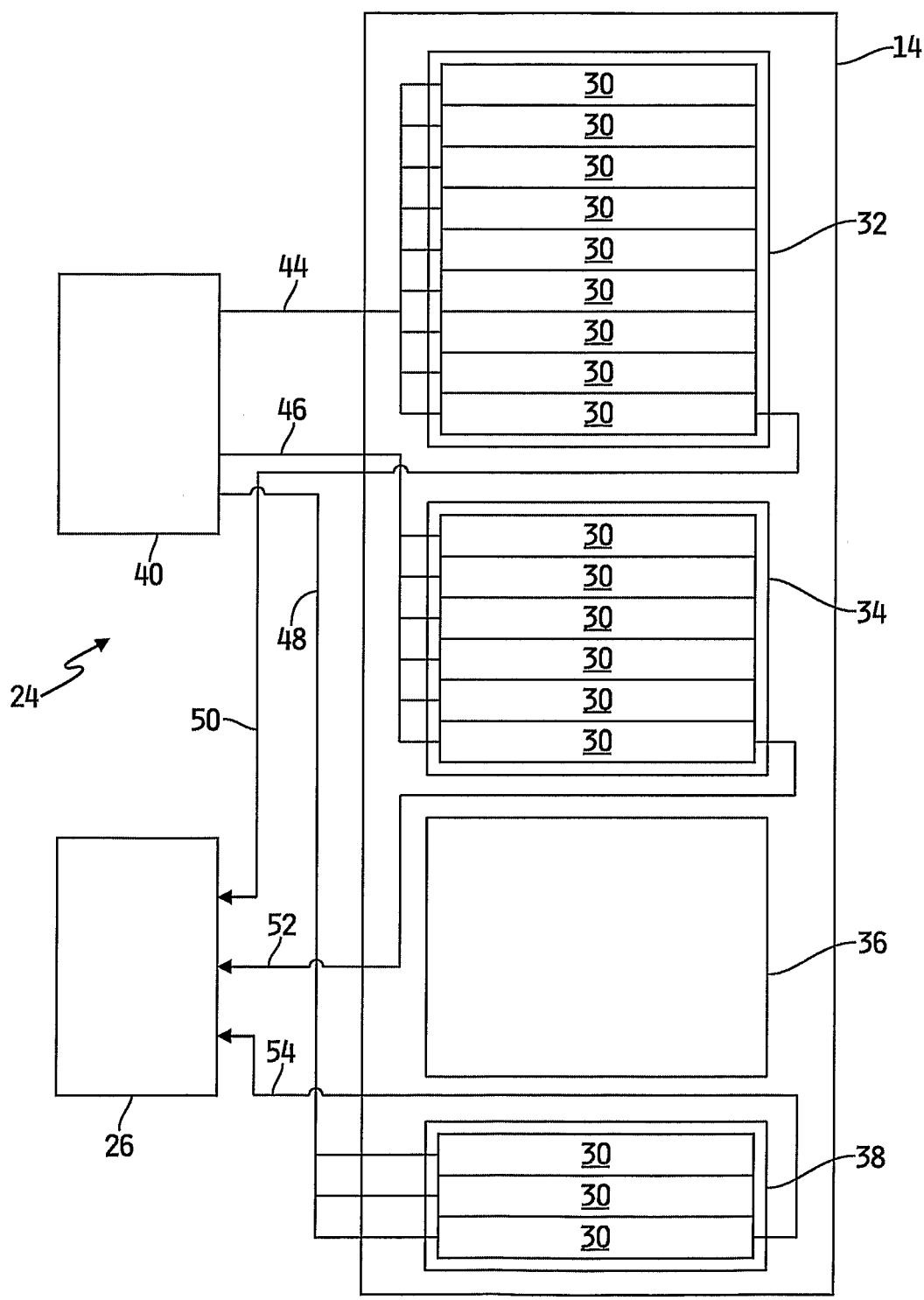
FIG. 3 is a diagrammatic view of an air system associated with a mattress of the hospital bed of FIG. 1.
Figure 4:
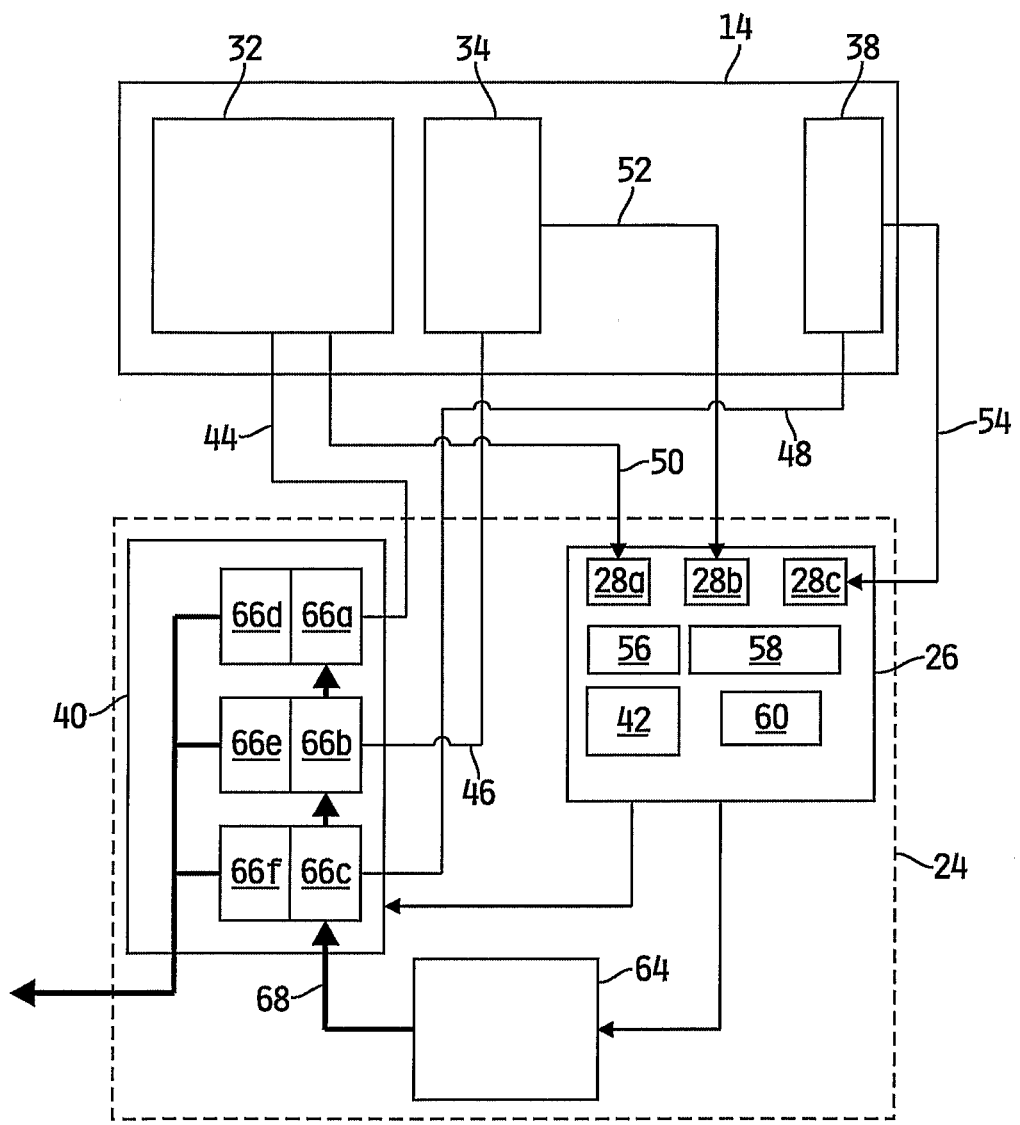
FIG. 4 is a diagrammatic view of the relationship between components of an air system controller of the air system of FIG. 3 and the mattress.

A patient support apparatus such as a hospital bed 10, for example, includes a frame 12, a mattress 14, and multiple siderails 16, 18, 20, 22 as shown in FIG. 1. The mattress 14 is supported on the frame 12. In the illustrative embodiment, hospital bed 10 is a VersaCare™ bed marketed by Hill-Rom Company, Inc. Referring now to FIGS. 3 and 4, the mattress 14 includes multiple air bladders 30 which are inflated by an air delivery system 24 (best seen in FIG. 4) which is coupled to the frame 12 and in fluid communication with the mattress 14. The air delivery system 24 includes an air system controller 26 which utilizes information from three pressure sensors 28a, 28b, 28c in fluid communication with the air bladders 30 and which provide a signal to the air system controller 26 indicative of the air pressure in the bladders 30. As will be described in detail below, the pressure in the air bladders 30 is controlled by the air system controller 26 to adjust an interface pressure between the patient and the mattress 14.

While the illustrative embodiment includes multiple bladders on a patient support such as a hospital bed or hospital bed mattress, the disclosure contemplates supports having any of a number of bladders, including at least one bladder. Also, the disclosure is equally applicable to person supports used in environments other than a hospital setting, including chairs, sofas, beds and the like. Additional details of the VersaCare™ bed, which is the embodiment illustrated herein, may be found in U.S. Pat. No. 6,691,346, which is hereby incorporated herein by reference.

The air system controller 26 is programmed with software to monitor pressure in a respective bladder 30 over time and analyze the time based relationship of the air pressure in the bladders 30 to make decisions as to target pressures to be set in various bladders 30 of the mattress 14. By monitoring the time based relationship of the pressures in the mattress bladders 30, the software determines which of the bladders 30 are predominantly supporting the patient and adjusts the target pressures of the bladders 30 to adjust the interface pressures between the mattress 14 and a patient supported on the mattress 14.

As shown in FIG. 3, the illustrative mattress 14 is divided into four support zones; a head section zone 32, a seat section zone 34, a leg section zone 36, and a foot section zone 38. Head section zone 32 supports the upper body of a patient residing on the mattress 14. The seat section zone 34 supports the buttocks and upper thigh portion of a patient on mattress 14. Leg section zone 36 supports the patient's legs in the mid thigh through the calf area. The foot section zone 38 supports the heels of a patient lying in a supine position on the mattress 14. The head section zone 32, the seat section 34, and the foot section zone 38 each have inflatable bladders 30 which serve as support structure for the patient in those areas. Leg section zone 36 of the illustrative embodiment has foam material and does not provide any active pressure management. In one embodiment, the foam material is perforated to allow the foam to expand and retract along the longitudinal dimension of the foot section as the foot section is lengthened or shortened by mechanisms included in hospital bed 10. It should be understood that, in other embodiments, the foam material may be omitted and replaced with air bladders to provide support and pressure management for the patient in that area. Mattresses having any number of inflatable support zones, not just four zones, are contemplated by this disclosure.

In the illustrative embodiment, head section zone 32 includes nine air bladders 30 oriented transversely to a longitudinal length of the hospital bed 10 with all of the bladders 30 plumbed together to form a single closed volume in head section zone 32. Similarly, seat section zone 34 comprises six transverse bladders 30 plumbed together so that the bladders 30 form a single closed volume. Also, foot section zone 38 comprises four bladders 30. Multiple bladders 30 are used in each zone in order to distribute support of the patient over multiple structures. Each of the bladders 30 are subject to the same target pressure. The target pressure is substantially equal across all bladder in each zone but the use of multiple bladders 30 provides multiple structures to support a patient's body in a particular zone.

In the illustrative embodiment, the zones 32, 34, and 38 each have a conduit, illustratively embodied as a hose, which communicates between the zone and a manifold 40 of the air delivery system 24 with each hose for each zone being connected to each bladder in the zone. Hose 44 is in communication with head section zone 32, hose 46 is in communication with seat section zone 34, and hose 48 is in communication with foot section zone 38. In addition, each zone 32, 34, and 38 has an independent sense line which senses and communicates the pressure in the zone between the respective zone and a pressure sensor 28 dedicated to the zone. Sense line 50 is in communication with head section zone 32, while sense line 52 is in communication with seat section zone 34, and sense line 54 is in communication with foot section zone 38. In the illustrative example, the sense lines are connected to ends of the bladders 30 opposite the ends to which the hoses 44, 46, and 48 are connected, but this need not be the case. Through empirical study it has been found that the use of distal sensing or, in other words, sensing a pressure at a point distal to the hose delivering pressurized air results in improved performance of a pressure based feedback control system such as the system employed in the illustrative embodiment, but again, this arrangement is optional.

The air system controller 26, the manifold 40, and a compressor 64 are all included in the air delivery system 24 as shown diagrammatically in FIG. 4. The air system controller 26 is electrically coupled to the compressor 64 and the manifold 40. The manifold 40 includes six valves 66a, 66b, 66c, 66d, 66e, and 66f, with valves 66a, 66b, and 66c operating as fill valves and valves 66d, 66e, and 66f operating as vent valves. The fill valves 66a, 66b, and 66c control the flow of air from a conduit, illustratively embodied as hose 68, to each of the respective support zones 32, 34, and 38. The vent valves 66d, 66e, and 66f each control the venting of the respective support zones 32, 34, 38 to atmosphere. Each of the sense lines 50, 52, 54 communicates with respective pressure sensors 28a, 28b, and 28c. In the illustrative embodiment, the pressure sensors 28a, 28b, and 28c are part number MPXV5010GC7U pressure transducers available from Motorola, Schaumburg, Ill.

Figure 5:
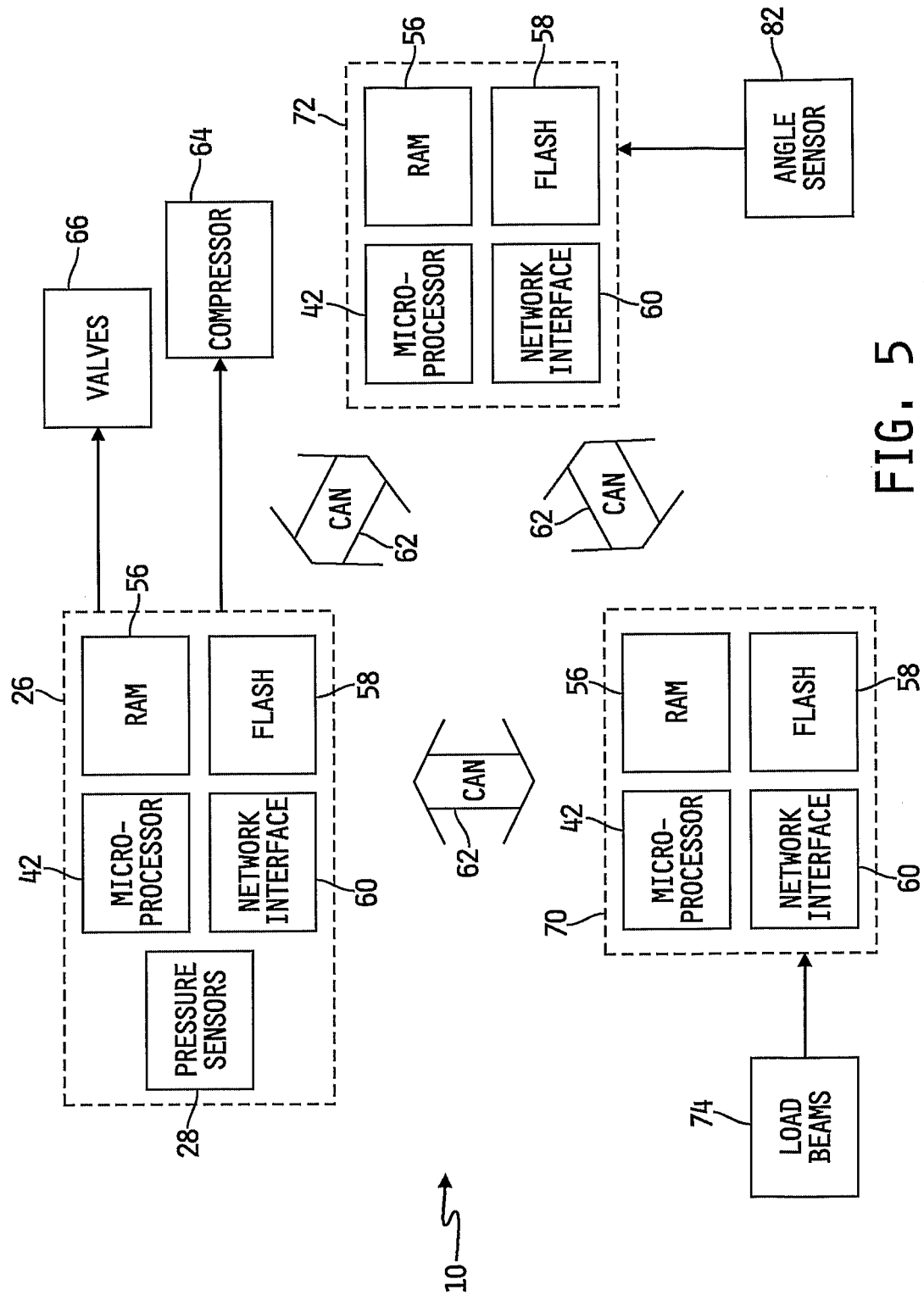
FIG. 5 is a diagrammatic representation of the relationship of various portions of a controller area network (CAN) of the hospital bed of FIG. 1.

The air system controller 26 utilizes a part number AT89C51CC03 microprocessor from Atmel Corporation, San Jose, Calif. and which includes processor 42, random access memory 56, volatile memory 58, and a network interface 60. In the illustrative embodiment, the air system controller 26 is part of a controller area network (CAN) 62 as illustrated in FIG. 5. Hospital bed 10 has multiple CAN nodes which provide distributed control of the various functions and features of the hospital bed 10. In the illustrative embodiment, the transducers 28a, 28b, and 28c are pneumatically coupled to zones 32, 34 and 38 and electrically coupled to the processor 42.

The air system controller 26 operates locally to set target pressures in each of the support zones 32, 34, and 38 and to control the air delivery system 24 to maintain the pressure in each of the support zones 32, 34, and 38 utilizing the target pressures as set points and controlling the opening and closing of the valves 66a-66f and the operation of compressor 64 to achieve the target pressures within a tolerance range. The air system controller 26 relies on the pressures sensed by pressure sensors 28a-28c along with elapsed time to perform the pressure control analysis. Additionally, the air system controller 26 relies on information provided by other nodes on the CAN 62. As can be seen in FIG. 5, the hospital bed 10 includes a scale system controller 70 and a logic module 72. The scale system controller 70 and logic module 72 are configured similarly to the air system controller 26 and each include a processor 42, RAM 56, volatile memory 58, and a network interface 60. The air system controller 70, scale system controller 70, and logic module 72 communicate via the CAN 62 and are thereby electrically connected.

Figure 2:
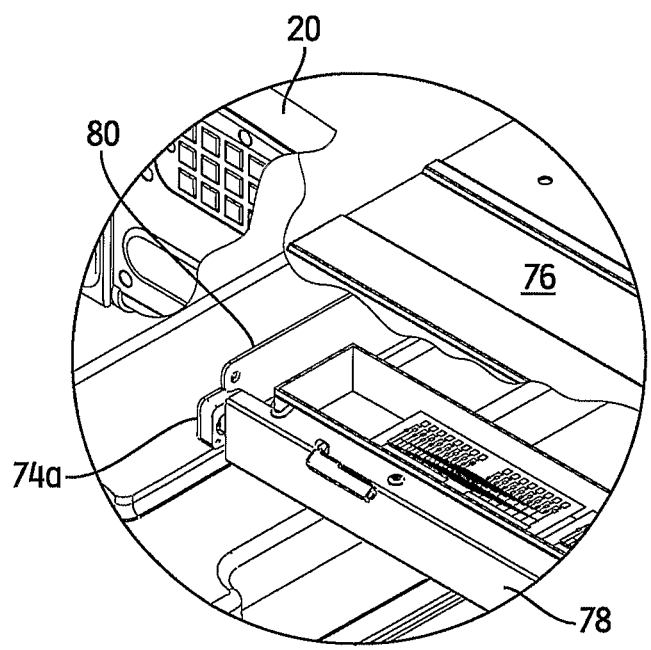
FIG. 2 is an enlarged view of the hospital bed of FIG. 1 with portions cut away to illustrate the location of load cells in the hospital bed frame.
Figure 6:
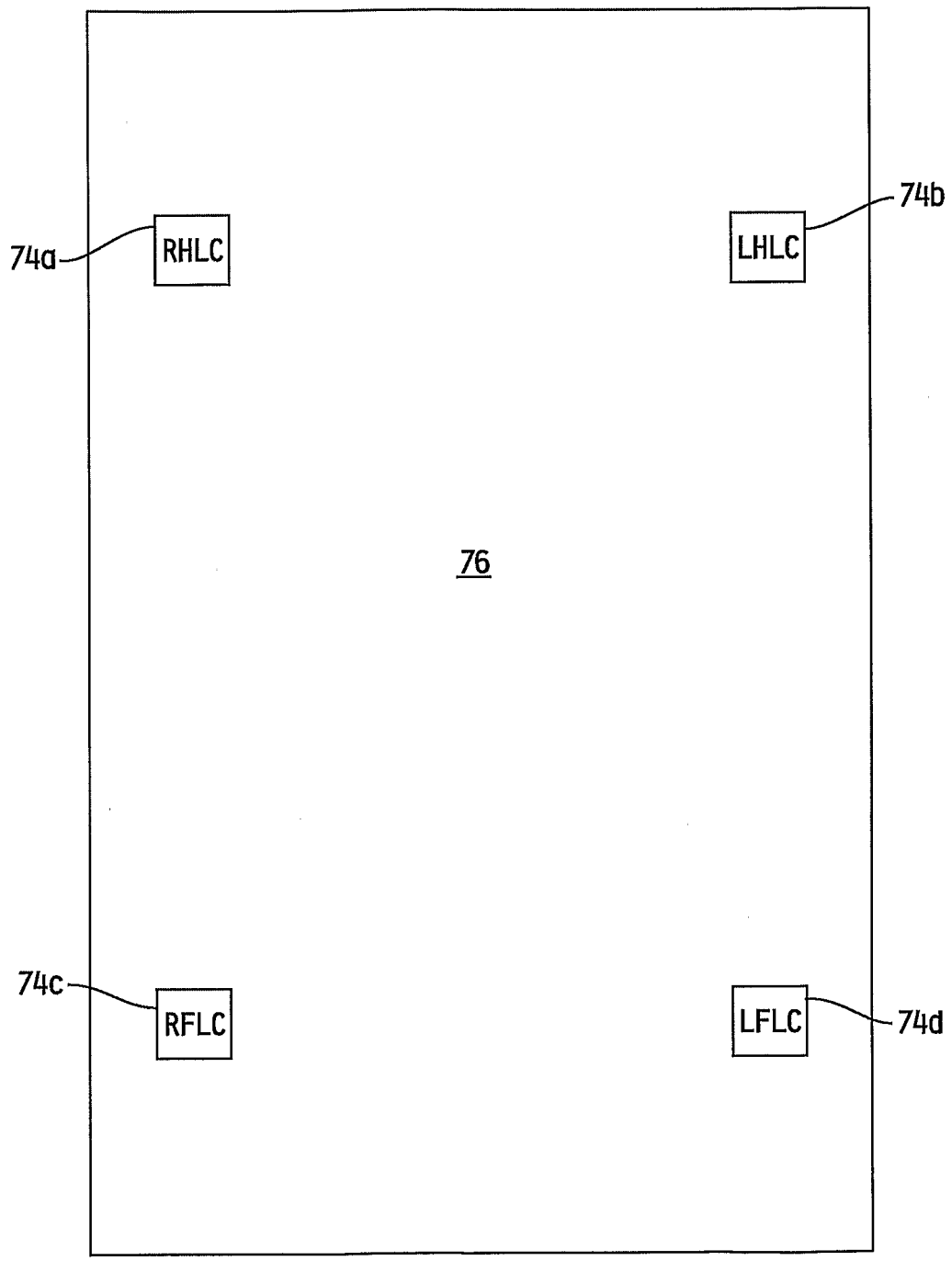
FIG. 6 is a diagrammatic representation of the location of various load cells to a support deck of the hospital bed of FIG. 1.

The scale system controller 70 receives information from weight sensors, such as, illustratively, four load beams 74a, 74b, 74c, and 74d which is converted by the scale system controller 70 to a patient weight utilizing methods known in the art. The weight of the patient is supported on the load beams 74a, 74b, 74c, and 74d such that the signal from the load beams 74a, 74b, 74c, and 74d is indicative of the weight. For example, the location of the load beam 74a within frame 12 is shown in FIG. 2. Frame 12 includes a support deck 76 which supports mattress 14. Support deck 76 comprises multiple members or sections that articulate relative to an upper frame 78. Upper frame 78 is supported relative to intermediate frame 80 on four load beams 74a, 74b, 74c, and 74d. The remaining load beams 74b, 74c, 74d are all mounted between upper frame 78 and intermediate frame 80 in a manner similar to load beam 74a. The location of the load beams 74b, 74c, 74d relative to the support deck 76 is shown diagrammatically in FIG. 6.

Figure 7:
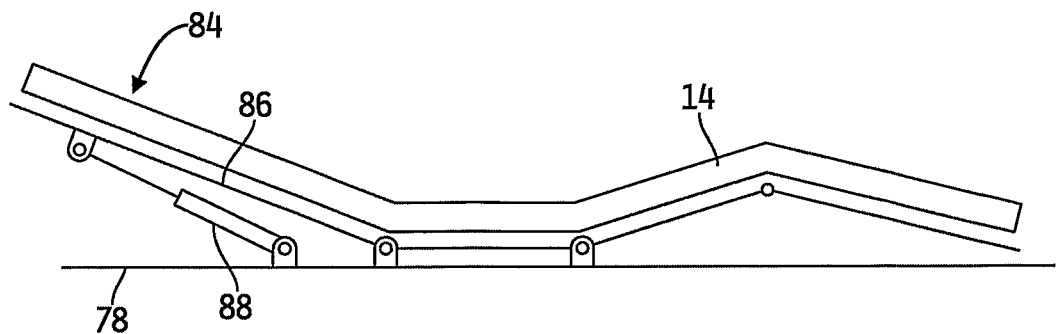
FIG. 7 is a side view of the hospital bed of FIG. 1 with portions cut away, the side view illustrating the relationship of a head portion drive to a head portion of a support deck of the hospital bed of FIG. 1.

The logic module 72 receives a signal from an angle sensor 82 to determine the relative angle of inclination of a head section 84 (best seen in FIG. 1) of mattress 14. Referring now to FIG. 7, the head section 84 is inclined by the articulation of a head portion 86 of support deck 76 relative to the upper frame 78. The articulation is driven by a linear actuator 88 in the illustrative embodiment. The linear actuator 88 includes a potentiometer (not shown) which is driven by a motor (not shown) of the linear actuator 88. Rotation of a drive wheel of the potentiometer changes the resistance value of the potentiometer and thereby provides an indication of the length of linear actuator 88. The length of linear actuator 88 is correlated by the controller 26 to an angle of articulation of head portion 86 relative to upper frame 78 and the resulting angle of articulation of head section 84 of mattress 14. In some embodiments, other devices may be used to provide a signal indicative of the articulation of a section of the patient support. For example, an accelerometer, a ball switch, limit switches, or other devices may be used to indicate articulation of a section.

The angle of articulation and patient weight data are available on the CAN 62 as network messages and are therefore available to the air system controller 26. The air system controller 26 utilizes the angle of articulation, the patient weight, and the pressure sensed in the support zones 32, 34, and 36 to analyze the operations of the air delivery system 24 and to determine what control activities, if any, are indicated. The air system controller 26 includes software resident in RAM 56 to perform the algorithms necessary to control air delivery system 24. The parameters controlled are activation of the various valves 66a-66f and the operation of compressor 64.

Illustrative valves 66a-66f are solenoid valves which are normally closed and which are energized to allow flow through the valve. In the illustrative embodiment, the solenoid valves are part number SY-124-6HZ-X70 valves available from SMC Corporation of America, Indianapolis, Ind. In the illustrative embodiment, air compressor 64 is a part number 6025 SE air compressor available from Thomas, Inc., Sheboygan, Wis. The air system controller 26 acquires data from the various inputs (i.e., angle sensor 82, pressure sensors 28a-28c, and load beams 74a-74d) through the network at regular intervals, processes the information from these inputs, and signals the outputs (i.e., valves 66a-66f and compressor 64) appropriately. The air system controller 26 software transitions between states as necessary to control the air delivery system 24, with each state representing a different control routine.

Figure 8:
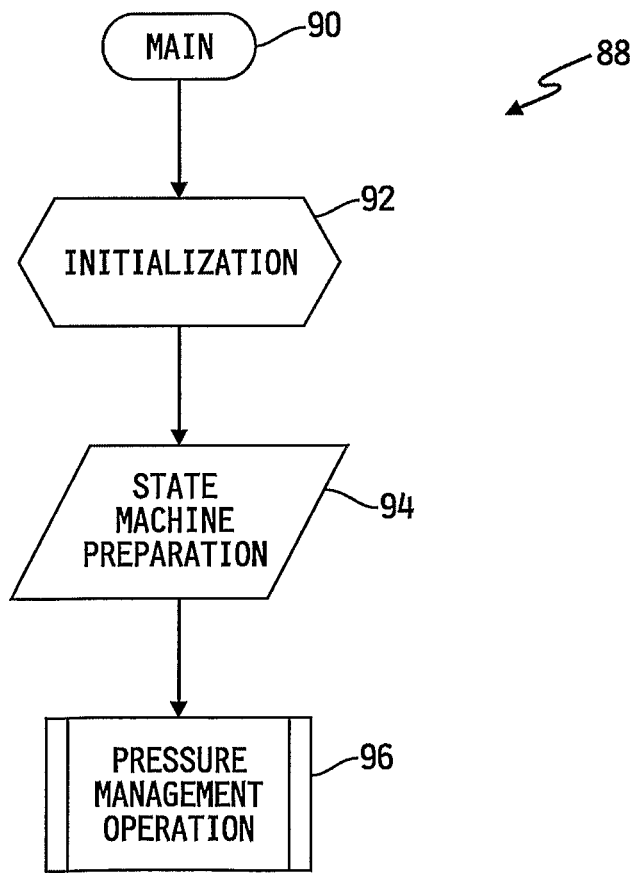
FIG. 8 is a flowchart of the initialization of software associated with control of an air mattress of the hospital bed of FIG. 1.

The CAN 62 has a central scheduler which schedules the activities of various control routines within the hospital bed 10 operating system. The scheduler assures the integrity of global variables utilized by the various nodes of the CAN 62 and allocates network resources to the various nodes. Focusing on the control routines of the air system controller 26, a diagram of an initialization routine 88 of the air system controller 26 is shown in FIG. 8. The initialization routine 88 is called by a main control routine 90. Upon being called, an initialization step 92 is performed where global variable values are set in the air system controller 26. Initialization step 92 is followed by preparation of the air system controller 26 state machine at step 94 where the parameters of the system start-up, such as conditions of reset, are considered and a mode of operation is selected consistent with those parameters. Once the variables are initialized and the state machine is prepared, the pressure management operation control 96 routine is entered.

Figure 9:
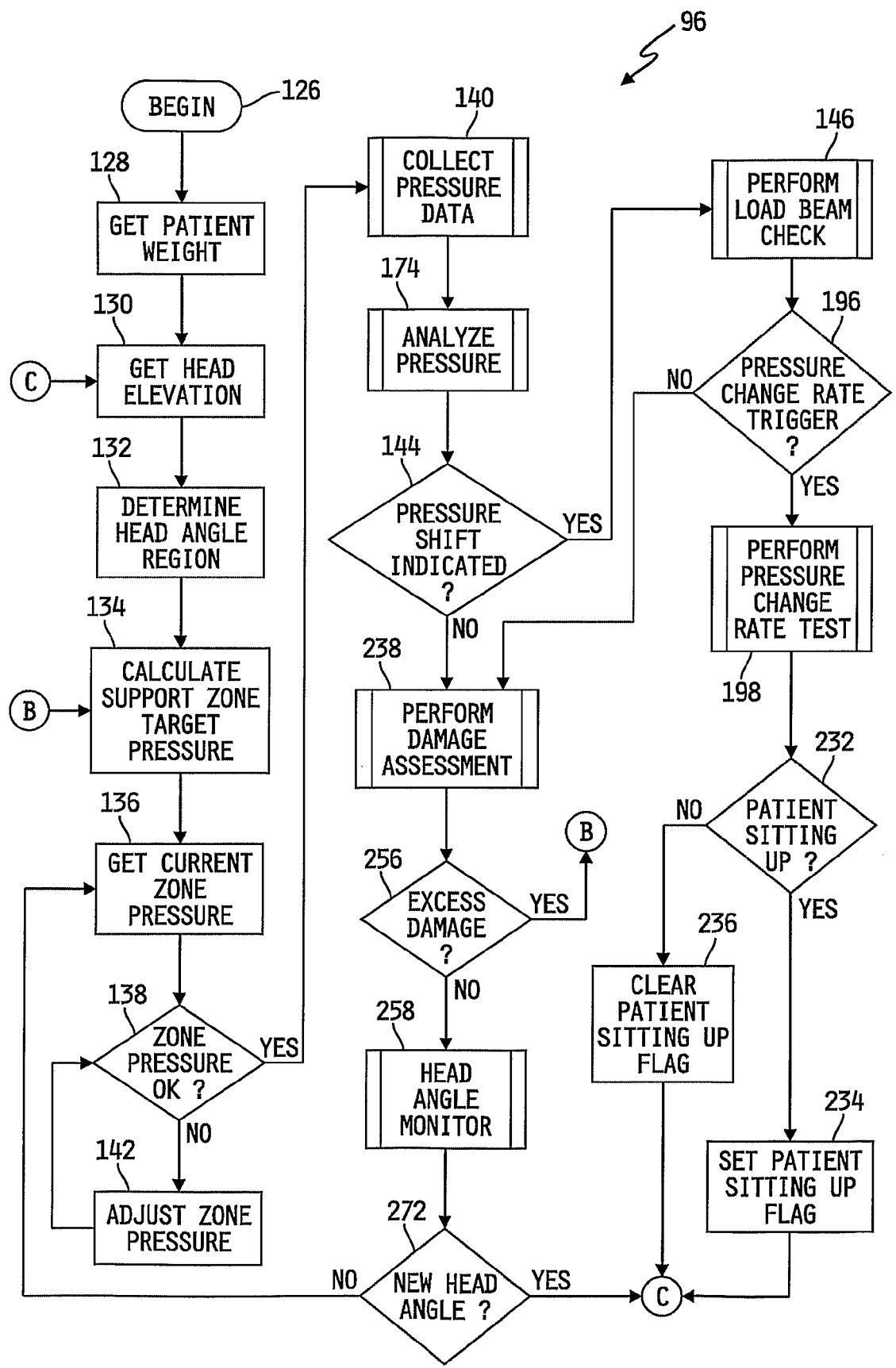
FIG. 9 is a flow chart of a software control routine of the air system controller of FIG. 4.

After step 94, shown in FIG. 8, the air system controller 26 commences the pressure management operation control routine 96 as indicated at block 126 shown in FIG. 9. As will be discussed in further detail below, the air system controller 26 considers patient weight, an articulation position of the patient support, a skin damage flag, and a patient sitting up flag to determine a target pressure for each of the zones 32, 34, and 38. The equations for calculation of target pressures are in the form of:

When the Patient is Laying Down $$\text{Head Target} = ((C1 \times \text{Patient Weight}) + C2) \times \text{Articulation Factor 1}$$

$$\text{Seat Target} = ((K1 \times \text{Head Target}) + (K2 \times \text{Patient Weight})) \times \text{Articulation Factor 2}$$

$$\text{Heel Zone Pressure Target} = H1 \times \text{Patient Weight} + H2$$

When the Patient is Sitting Up $$\text{Head Target} = C3 \times \text{Patient Weight}$$

$$\text{Seat Target} = K3 \times \text{Patient Weight}$$

$$\text{Heel Target} = H1 \times \text{Patient Weight} + H2$$

When Damage Flag is Set $$\text{Head Target Damage} = \text{Head Target} + (D1 \times \text{Head Target})$$

$$\text{Seat Z Target Damage} = \text{Seat Target} + (D2 \times \text{Seat Target})$$

where C1, C2, C3, D1, D2, H1, H2, K1, K2, Articulation Factor 1 and Articulation Factor 2 are all coefficients that vary depending upon one or more parameters such as patient weight, articulation angle, or amount of deviation from a target pressure.

The previous status of these conditions (i.e., patient weight, articulation position, skin damage flag, and patient sitting up flag) are used at start-up before the air system controller 26 begins pressure management control routine 96.

The air system controller 26 gets the load beam data indicative of patient weight from the scale system controller 70 at step 128 and the head elevation data from the logic module 72 at step 130. The air system controller then determines, at step 132, in which head angle region the head section is positioned. The head angle region evaluation is a tabular look up which determines a particular factor to use in the calculation of target pressures based on the position of the head angle and the most recent direction of travel of the head portion 86 of support deck 76. An illustrative example of the use of head angle intervals is that when the head section is raised, a first factor is applied from 0-10 degrees of elevation, a second factor is applied from 10-20 degrees of elevation, a third factor is applied from 20-30 degrees of elevation, a fourth factor is applied from 30-40 degrees of elevation, a fifth factor is applied from 40-50 degrees of elevation, a sixth factor is applied from 50-60 degrees of elevation, and a seventh factor is applied from 60-65 degrees of elevation. When the most recent direction of travel of the head section is lowering, the seventh factor is applied from 65-56 degrees of elevation, the sixth factor is applied from 55-46 degrees of elevation, the fifth factor is applied from 45-36 degrees of elevation degrees of elevation, the fourth factor is applied from 35-26 degrees of elevation, the third factor is applied from 25-16 degrees of elevation, the second factor is applied from 15-6 degrees of elevation, and the first factor is applied from 5-0 degrees of elevation.

The system considers direction of travel in order to compensate for angle sensing hysteresis in the head angle measurement. The combination of the head portion articulation linkage 86 and the head portion drive 88 have settling characteristics which permit the system to settle after the drive has stopped operation. The settling is affected by momentum such that a lowering head portion 86 will settle differently than a lifting head portion 86 which alters the hysteresis experienced.

At step 134 the air system controller 26 utilizes the patient weight information and head angle to calculate a target pressure for one of the support zones 32, 34, or 38. The description hereinafter will discuss the monitoring, analysis and control of a singular zone. It should be understood that the process is applicable to any of a number of support zones supporting a patient. The target pressure calculated represents a desired pressure which is believed to avoid injury to the patient's skin if the patient remains in a fixed position on the mattress 14 for an extended time.

When the air system controller 26 is adjusting to a new target pressure, an acceptable tolerance for the target pressure is established as discussed in detail below. The air system controller 26 adjust to a pressure that is within this acceptable tolerance. Specifically, at step 136 the air system controller 26 gets the current pressures in the zone read by the appropriate pressure sensor 28a, 28b, and 28c for the zone. At step 138, the actual pressure in the zone is compared to the target pressure calculated in step 134. If the actual pressure is within an acceptable tolerance of the target pressure, the control routine 96 advances to step 140. However, if the actual pressure is out of an acceptable tolerance band, the air system controller 26 adjusts the pressure in the zone at step 142.

This adjustment utilizes a proportional-integral-derivative (PID) control routine to control the operation of the compressor 64 and zone fill valve 66a, 66b, or 66c and vent valve 66d, 66e, 66f to adjust the pressure in the zone to be within an acceptable tolerance of the target pressure for the zone. Once a target pressure is calculated, the system determines a related bogey pressure. The bogey pressure is developed as an "overshoot" value. If the system is inflating a zone, the bogey pressure is set slightly greater than the target pressure. In the illustrative embodiment, the bogey pressure is set at 0.5 inches of water (0.93 mm of mercury) greater than the target pressure. As the system inflates the zone, the pressure in the zone is monitored until the bogey pressure is reached. At that point, inflation is halted. Once the zone has had time to settle, the system checks the actual pressure and compares the actual to the target to confirm that the actual pressure is within an acceptable tolerance of the target. The bogey pressure is set slightly lower than the target pressure when the system is in the deflate mode. In the illustrative embodiment, the bogey pressure is set at 0.5 inches of water (0.93 mm of mercury) less than the target pressure. The use of the bogey pressure allows for hysteresis in the system as the pressure is changing. Empirical evidence has shown that the offset between the bogey and the target results in an actual pressure within an acceptable tolerance of the target.

The tolerance band size in chosen to provide effective pressure management while reducing the potential for dithering of the PID control routine. For example, a tolerance of about +/−0.75 inches of water (1.4 mm of mercury) provides a reasonable tolerance from the target. Upon completion of the adjustment loop between steps 138 and 142, the pressure management control routine 96 advances to step 140.

In the software algorithm example of FIG. 9, the adjustment of the head section zone 32, seat section zone 34 and foot section zone 38 pressures are sequential processes. It should be understood that these processes may occur simultaneously through proper application of the air system controller 26 processor 42 scheduling approach. The description of the processes occurring in a sequential fashion is for illustrative purposes only. Those skilled in the art will readily recognize that a control routine may be implemented which minimizes the time to adjust all of the zones by sharing of the pressurized air from the compressor 64 and appropriate management of the valves 66a, 66b, 66c, 66d, 66e, and 66f.

Step 140 diagrammatically represents a subroutine which collects pressure data from the zone to be utilized by the pressure management control routine 96 in responding to changes in the inputs to the air system controller 26. The subroutine 140 is presented in FIG. 10A. Subroutine 140 operates continuously with the processor 42 scheduler multi-tasking to call subroutine 140 at regular intervals. At step 156, the collect pressure data subroutine 140 captures the current zone pressure, at step 158, the zone pressure data buffer is shifted in a first in first out (FIFO) fashion create a memory location for the latest pressure data point. At step 160, the new zone pressure data point is written to the buffer. Subroutine 140 maintains the pressure data for use by other subroutines of the pressure management control routine 96. The size of the pressure data buffer may be selected so as to provide a sufficient sample size to perform statistics over the particular sample period. This period may be as small as a few milliseconds or as large as several minutes. In one exemplary embodiment, a polling rate of once every 20 ms and a buffer size of thirty data points is used.

Figures 10A, 10B:
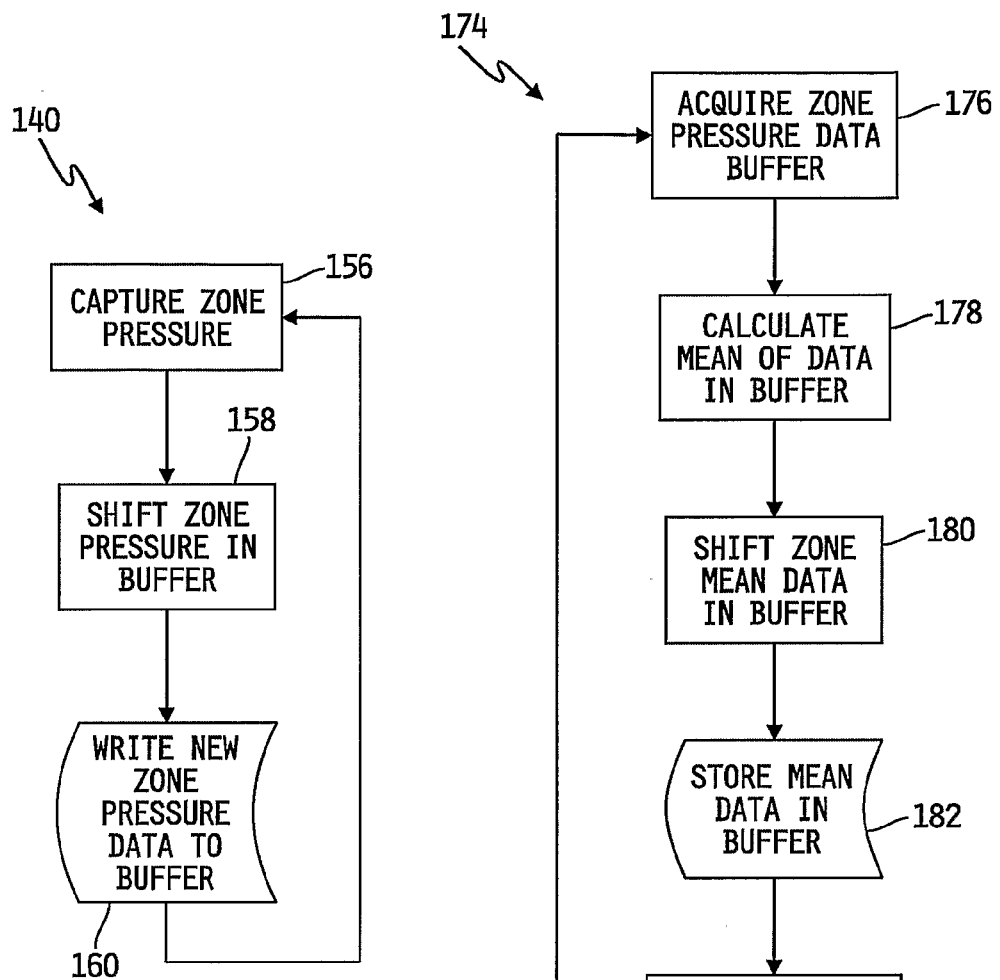
FIG. 10A is a flow chart of a data management subroutine used to store pressure data associated with the operation of the mattress of FIG. 3.
FIG. 10B is a flow chart of a data management subroutine used to perform and store statistical information based on the data captured in the subroutine of FIG. 10A.

The pressure management control routine 96 calls another subroutine at step 174. Subroutine 174, shown in FIG. 10B, is a pressure analysis subroutine which calculates statistics on data in the pressure data buffer. The pressure analysis subroutine 174 also operates continuously with the processor 42 scheduler multi-tasking to call subroutine 174 at regular intervals to perform the calculations. At step 176, the pressure analysis subroutine 174 acquires the data from the pressure data buffer. At step 178, subroutine 174 calculates the sample mean of the data points in the data buffer. At step 180, the mean data stored in a mean data buffer is shifted to make room for the new sample mean. At step 182, the new mean sample data point is stored in the buffer. At step 184, the analyze pressure subroutine 174 calculates the standard deviation of the data in the buffer. At step 186, the buffer storing sample standard deviation data is shifted in a FIFO fashion to make room for the new sample standard deviation data. At step 188 the data point is stored in the data buffer. In one exemplary embodiment, the statistical calculations are made once every 600 ms. This calculation rate, along with the data capture rate of the collect pressure data subroutine 140 described above, provides sample statistics on zone pressure data of a sample size of six data points. Additionally, the sample statistics buffer sizes for both the mean and sample standard deviation is six data points each. Therefore, data is available for the zone pressures for the previous 3.6 seconds, at any given time.

While the illustrative embodiment of control routine 96 shown in FIG. 9 shows the check pressure data subroutine 140 and analyze pressure subroutine 174 being conducted in a sequential fashion, it should be understood that the scheduler of processor 42 may multi-task the processor to operate the subroutines continuously. Therefore, at any given time, the data from the subroutines is available to be used by other processes and subroutines of pressure management control routine 96.

Figure 12:
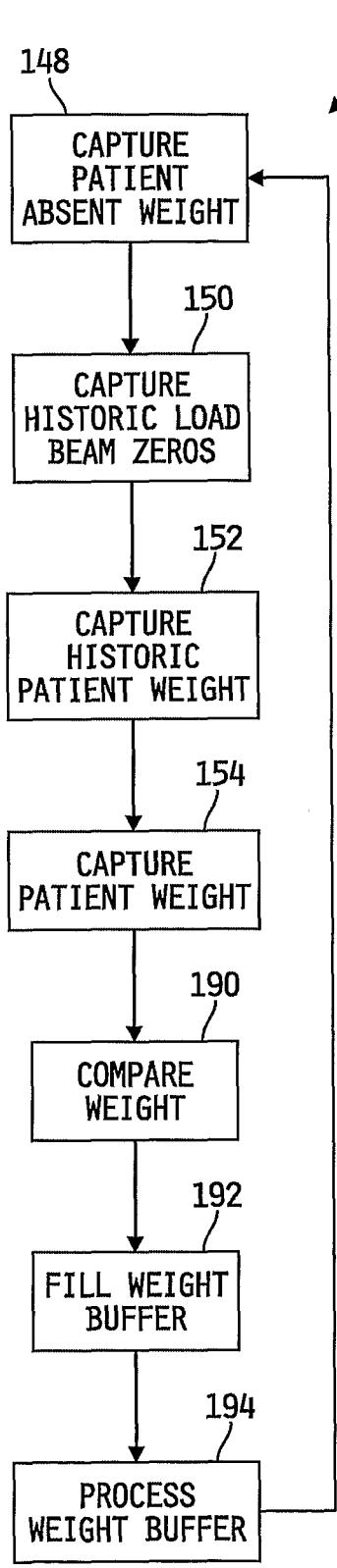
FIG. 12 is a flow chart of a load beam check subroutine used to analyze load beam data associated with the load beams of FIG. 6.

Pressure management control routine 96 evaluates the historical information of the pressure in the zone at step 144. Step 144 is a decision step which evaluates whether a pressure shift has been indicated in the zone based on the statistics developed in the analyze pressure subroutine 174. In one exemplary embodiment, the decision as to whether or not a pressure shift is indicated is based on the change in the mean pressure in the zone on an absolute pressure basis. In other embodiments, the pressure shift analysis may utilize any of a number of other statistical techniques such as a t-test, F-test, or the like. If a pressure shift is indicated at step 144, pressure management control routine 96 advances to step 146 which is a subroutine for performing a load beam check and is shown in FIG. 12. The load beam check subroutine 146 captures the patient absent weight at step 148. The patient absent weight is the tare weight measured at each beam independently when a patient is known to be absent from the hospital bed 10. At step 150, load beam check subroutine 146 captures the historical load beam zeros which are the correction values or beam constants which represent the offset in the beams due to electrical and mechanical variation. This information allows the load beam data to be compensated for the built-in error that exists in the beam. At step 152 load beam check subroutine 146 captures the stored patient weight data from the scale system controller 70. This data is provided on a beam by beam basis and the system to sums the values sensed by each of the load beams in the scale system to arrive at an actual total patient weight.

At step 154, the actual patient weight is captured by the perform load beam check subroutine 146. Again, the weight captured is on a beam by beam basis. At step 190, the current patient weight captured at step 154 is compared to the historic patient weight captured at step 152 with adjustments made based on the patient absent weight gathered at step 148 and the historic load beam zeros gathered at step 150. Patient weight information developed at step 190 is stored in an information buffer at step 192. Information buffer maintains a comparison of the change in position of the patient on the mattress 14 as predicted by the load beam data. This is determined on a change basis. It should be noted that a patient's actual position (i.e., the location of the patient's center of gravity) is never calculated. The information in the information buffer is processed at step 194 to develop data which may support or contradict the possibility that a patient has changed position along the longitudinal length of the hospital bed 10. Similarly to subroutines 140 and 174, subroutine 146 called by the scheduler of the processor 42 which continuously multi-tasks the processor 42. The data developed by a subroutine 146 is available for analysis by the pressure management operation control routine 96.

If a potential pressure shift was indicated at step 144, and the data from load beam check subroutine 146 supports the pressure shift decision at step 144, a pressure change rate test may be triggered at decision step 196. Decision step 196 evaluates the information from both the analyze pressure subroutine 174 and the load beam check subroutine 146 weighing the data available to determine that a pressure change rate trigger is justified. In the illustrative embodiment, a change rate trigger may be justified if the combination of the pressure shift and the load beam information statistically supports an inference that the patient resident on the mattress has sat up. This decision is based on the magnitude of the pressure shift and the magnitude of the change in the weight distribution of the patient on the load beams longitudinally on hospital bed 10. An equation in the form of:

$$(K_1 \times \text{Pressure Shift}) + (K_2 \times \text{Weight Shift}) = \text{Likelihood} \qquad \text{(Equation 1)}$$

is calculated. In this equation $K_1$ is a predefined value based on the patient weight and the last known patient position. $K_2$ is also a predefined value based on the patient weight. The values are stored in lookup tables which are accessed by the air system controller 26. The weighting of the pressure shift as compared to the weight shift varies depending on the patient weight. For example, $K_2$ may be larger for a 100 pound patient then for a 250 pound patient. Similarly, $K_1$ may be smaller for a 100 pound patient as compared to a 250 pound patient. Typically, the Likelihood value is driven mostly by $K_1$ and the pressure shift. In some embodiments, the load beam check and weight shift may be omitted and the decision to trigger a pressure change rate test may be entirely dependent on the magnitude of the pressure shift. See pages 144-150 of Appendix 2 and pages 18-45 of Appendix C of U.S. Provisional Patent Application 60/702,645, which is incorporated by reference herein, for a specific example of the K1 and K2 values and the approach described herein as executed in the VersaCare™ product.

Figure 13:
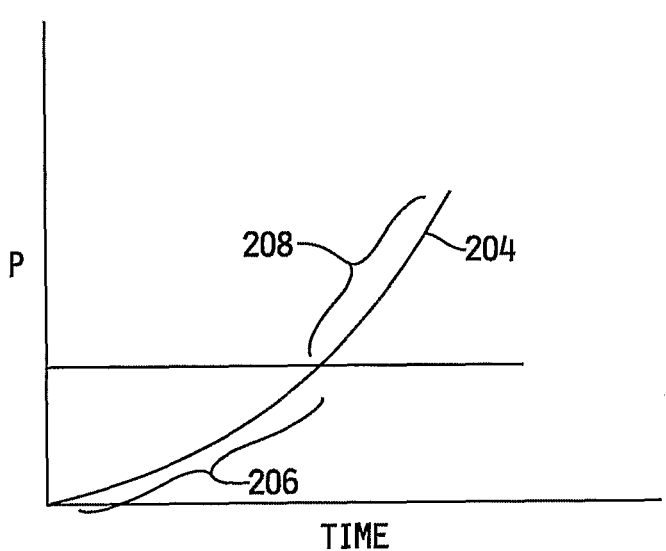
FIG. 13 is a graphical representation of pressure as a function of time within a bladder of the mattress of FIG. 3 during inflation of the bladder.

If the Likelihood calculated in Equation 1 exceeds a threshold value, a pressure change rate test subroutine 198 is called. The subroutine 198 is a test that is performed to evaluate whether or not the patient is present on the particular zone being evaluated based on a pressure signal. Subroutine 198, shown in FIG. 11, begins at step 200 by initiating a timer. Subroutine 198 advances to step 202 where an inflation rate zone test is initiated. The purpose of this test is to evaluate the rate of pressure change which occurs in the zone to evaluate the presence of a portion of the patient on that zone. Referring to FIG. 13, a diagram of the pressure in an expandable volume is represented by the line 204. The region 206 is generally linear as the expandable volume is filled as a greater and greater pressure is required to expand the volume. Once the expandable volume has reached an elastic limit, the pressure increases much more rapidly over time because additional air no longer expands the bladder volume, once the bladder is fully inflated. The derivative of the curve 204, dP/dt, is the instantaneous slope of the curve at any point in time. A transition of the curve from the portion 206 to the portion 208 results in a change in the slope of the curve dP/dt. By comparing the slope of the curve to a predetermined criteria, the transition of the expandable volume from a relatively elastic expansion to a relatively inelastic expansion can be detected. A bladder which supports an individual reaches the elastic limit more quickly than an unloaded bladder, so the air system controller 26 is able to discern that a load is applied to the bladder. Similarly, during deflation, a bladder under load deflates more rapidly as compared to an unloaded bladder as the weight of the individual tends to force air from the bladder.

Figure 11:
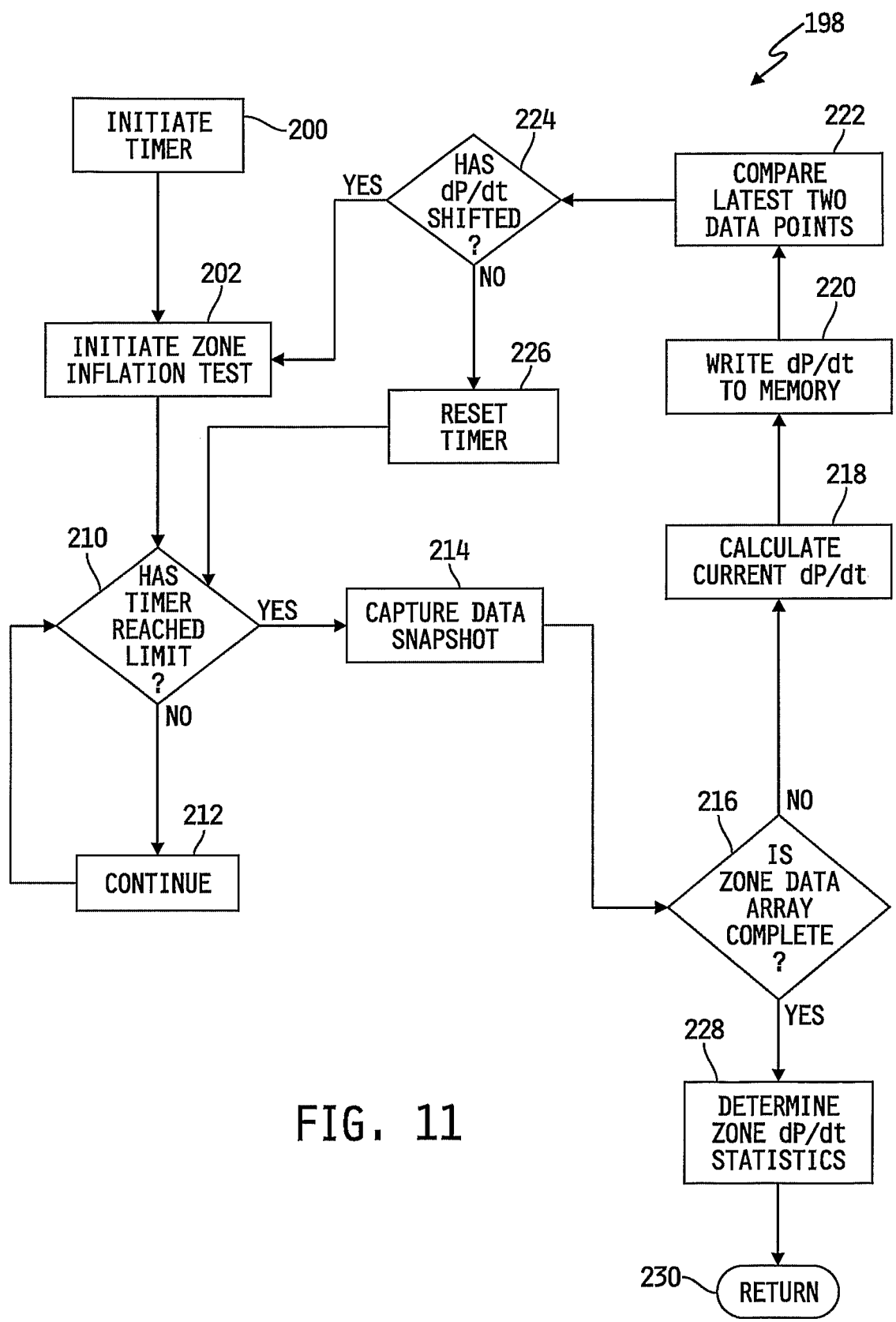
FIG. 11 is a flow chart of a pressure rate test subroutine used to analyze the pressure rate change within a bladder of the mattress of FIG. 3 during inflation of the mattress.

Referring now to FIG. 11, at step 210 the timer status is evaluated. If the timer has reached its limit, then subroutine 198 advances to step 214. If the timer has not reached its limit, the subroutine loops through step 212 which is a continue process and returns to decision step 210. This assures that pressure data is captured in specific, predetermined time intervals to assure the integrity of the calculations made within subroutine 198. In the illustrative embodiment, samples are taken at 20 millisecond intervals. At step 214, the subroutine captures the pressure data for the first time interval. The subroutine then advances to decision step 216 where an analysis of the data array size is made. In the illustrative embodiment the buffer includes thirty samples to provide a sufficient time window of data for analysis. If the sample is not complete then subroutine 198 advances to step 218 wherein instantaneous dP/dt is calculated by comparing the most recent data point to the previous data point to determine the change in pressure over the 20 ms interval. Subroutine 198 then advances to step 220 wherein the instantaneous dP/dt is written to memory. At step 222 the latest two dP/dt values are compared in a filter to assure that there has not been an unexpected shift in dP/dt. An unexpected shift in dP/dt may be caused by patient movement during the performance of the pressure change rate test. In other embodiments, other filtering techniques may be employed such as comparing the deviation of a current pressure to an initial pressure and determining that an unexpected shift has occurred based on the absolute difference in those pressure values. In addition, any of a number of other filtering techniques may be used to assure the data integrity during the pressure change rate test. At step 224 the subroutine 198 performs an error check to determine if an error indicative of a failure of the data integrity corrupting the pressure rate change test has occurred. If there has been a corruption, the subroutine 198 advances to step 202 and initiates the zone inflation test again which results in clearing of any data in the array and starting the tests from the beginning. If there has been no corruption detected by the filter the subroutine advances to step 226 wherein the timer is reset and the subroutine reenters the data collection stream at step 210.

If the subroutine determines that the data array is complete at step 216 then the subroutine advances to step 228 to determine the dP/dt statistics. Once the statistics are calculated the subroutine 198 returns to the pressure management control routine 96 at step 230. Pressure management control routine 96 then advances to step 232 as shown in FIG. 9, and utilizes the statistics developed by the perform pressure change rate test subroutine 198 to evaluate whether or not the patient is sitting up at decision step 232. In the illustrative embodiment, the first fifteen data points are averaged and the second fifteen data points are averaged. The difference of the two averages is taken and the difference is multiplied by two. This information is then analyzed to determine the position of the patient. For example, a dP/dt greater than a threshold value may be indicative that a patient is supported on the bladder. For example, if it is determined that the patient is not on the head zone 32, but the system otherwise concludes the patient is on the bed 10, (e.g., via the weight sensor readings) then this is indicative that the patient is sitting up.

By evaluating the dP/dt in any of the support zones 32, 34, or 38, the air system controller can assess the position of the patient on the mattress 14. In the illustrative embodiment, the pressure change rate test is utilized in the head section zone 32 and seat section zone 34. It should be understood that the pressure change rate test could be performed in the head section zone 32 only, seat section 34 only, foot section zone 38 only, or performed in any two or all three of the zones 32, 34 and 38 simultaneously to improve the accuracy of the patient position determination, if desired. The pressure rate change test may evaluate the dP/dt during inflation or during deflation in any one or all of the zones 32, 34, or 38. The statistics used in determining the patient position may include an average dP/dt, a linear regression of the dP/dt, a t-test, an F-test, an analysis of variance (ANOVA), or other statistical analysis. In each case, the system must first determine a dP/dt to determine if the change in dP/dt indicates a load is present or an elastic limit has been reached.

If a determination that the patient is sitting up is made at step 232 then the control routine 96 advances to step 234 and sets a patient sitting up flag. If the determination results in a finding that the patient is not sitting up, then be control routine 96 advances to step 236 and clears the patient sitting up flag. In either case, the control routine 96 returns to step 132. As discussed above, the patient sitting up condition is considered when determining the target pressure at step 134 of routine 96.

In some embodiments, historical changes in the pressure or pressure statistics may be used to determine that a patient has changed positions on one or more zones 32, 34, and 38. For example, while a patient may be continued to be supported on a zone 32, 34, or 38, a change in pressure may be indicative that a patient has rolled from a supine position to a side-lying position (i.e., the patient positioned on the patient support with the majority of their weight supported on their side as opposed to on their posterior in a supine position or anterior in a prone position).

When a patient moves to a side lying position, the weight of the patient is supported over a smaller area on the zone 32, 34, or 38. This results in a slight increase in pressure in the zone 32, 34, or 38 due to the movement. Also, an upper surface of the bladders 30 in the zone 32, 34, or 38 may deflect further due to a more centralized load on the surface of the bladder 30. A slight increase in pressure in the zone 32, 34, or 38 with no relative change in the distribution of the patient's weight along the longitudinal length of the hospital bed 10 may be inferred to be a result of a patient moving from a supine or prone position to a side-lying position.

Figure 15:
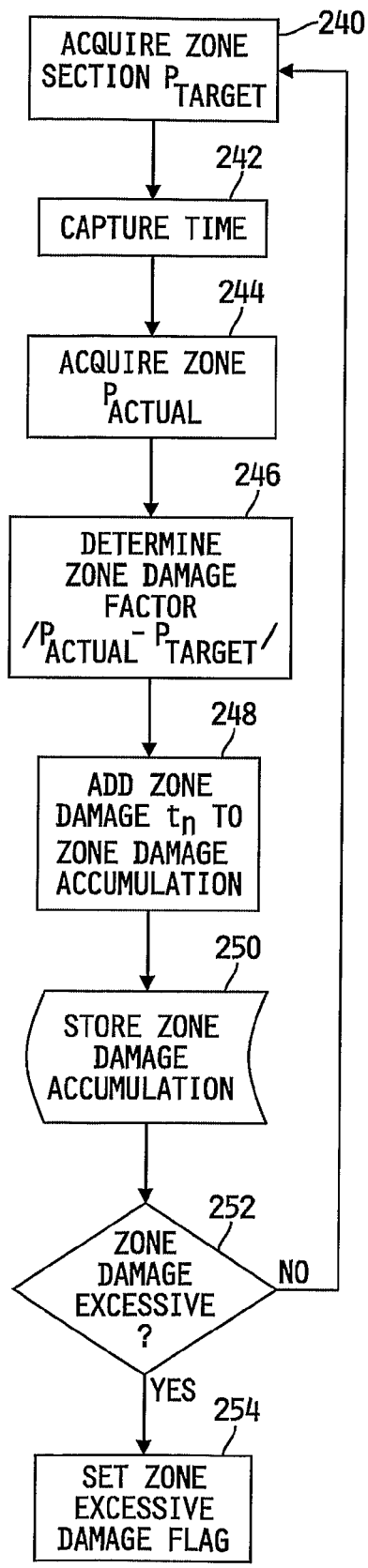
FIG. 15 is a flowchart of a damage accumulation subroutine used by software of the air system controller of FIG. 4 to analyze the potential for damage to the skin of a patient residing on the mattress of FIG. 3 due to variations from a target pressure in a bladder of the mattress.

If there was no pressure shift indicated at step 144 the control routine 96 advances to step 238 which is a perform damage assessment subroutine. Subroutine 238 is also a subroutine which the multi-task scheduler of the processor 42 calls regularly. Damage assessment subroutine 238 is shown diagrammatically in FIG. 15. The first step of the damage assessment subroutine 238 is step 240 where the subroutine 238 acquires the target pressure $P_{target}$ for the zone. Because the damage assessment is an accumulation of pressure deviation from the $P_{target}$, the subroutine must capture a time value which is performed at step 242. The subroutine 238 then advances to step 244 where the pressure in the zone, $P_{actual}$ is acquired from the appropriate pressure sensor 28a, 28b, or 28c.

Figure 14:
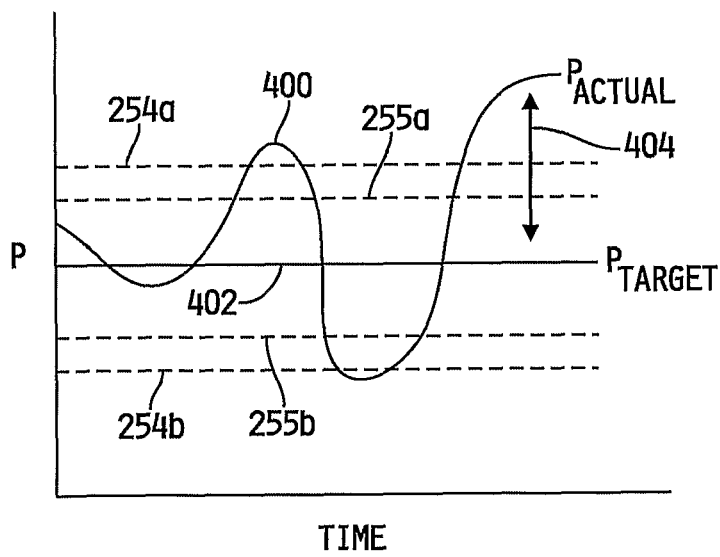
FIG. 14 is a graphical representation of an example of actual pressure as a function of time as it relates to a target pressure.

At step 246, subroutine 238 determines a damage factor which is determined by the value of $|P_{target}-P_{actual}|$, the absolute value of the difference between $P_{target}$ and $P_{actual}$. Referring to FIG. 14, an illustration of the variation of $P_{actual}$ as compared to $P_{target}$ over time illustrates the concept of a damage factor. $P_{actual}$ may deviate from $P_{target}$ due to slight changes in position of the patient or leaks in the air delivery system 24 which allows air to escape from the particular zone. Damage assessment subroutine 238 acquires data which is an approximation of the area between the $P_{actual}$ curve and the $P_{target}$ line. The area between the $P_{actual}$ curve and the $P_{target}$ line represents theoretical damage to the patient's skin due to the variation from the target pressure.

At step 248, the latest damage factor is added to the previously accumulated zone damage to update the total damage accumulation. At step 250 the new total damage accumulation is stored in memory and an evaluation of the theoretical damage in the applicable zone is performed at step 252 to determine if the damage is excessive (e.g., greater than a threshold). In the illustrative embodiment, a threshold value of damage for each particular zone is predefined based on a given patient weight. In other embodiments, the damage threshold may be variable for a given patient weight based on the deviation of $P_{actual}$ from $P_{target}$ on an absolute basis. For example, referring to FIG. 14, lines 255a and 255b represent a 30% variation from $P_{target}$ 402 and line 254a and 254b represent a 45% variation from $P_{target}$ 402. When $P_{actual}$ 400 exceeds the 30% tolerance bands 255a or 255b, the accumulation factor is multiplied by a weighting factor which results in a heavier weighting of the variation outside of the tolerance bands 255a and 255b. When $P_{actual}$ 400 exceeds the 45% tolerance bands 254a or 254b, the accumulation factor is be multiplied by a weighting factor greater than the weighting factor for the tolerance bands 255a or 255b. This approach provides an opportunity for greater damage accumulation if the variation of $P_{actual}$ 400 exceeds tolerance values. In some embodiments, the damage accumulation may be weighted differently for deviations above $P_{target}$ 402 than for deviations below $P_{target}$ 402. For example, damage above $P_{target}$ 402 may be weighted more heavily than deviations below $P_{target}$ 402 and the overall damage factor accumulated may be the sum of the two products according to the following equations:

For $P_{actual} > P_{target}$, Damage 1 = (D1×($P_{target} - P_{actual}$)) where D1 is a first weighting factor;

For $P_{actual} < P_{target}$, Damage 2 = (D2×($P_{actual} - P_{target}$)) where D2 is a second weighting factor; and Damage Accumulated = Damage 1 + Damage 2.

This approach accounts for differences in the extent of damage caused by variations above the $P_{target}$ compared to damage caused by variation below $P_{target}$. See pages 12-15 of Appendix 1, pages 131-132 of Appendix 2 and pages 232-238 of Appendix C of U.S. Provisional Patent Application 60/702,645, which is incorporated by reference herein, for a specific example of the weighting factors and the approach described herein as executed in the VersaCare™ product.

If it is determined at step 252 that the zone damage is excessive, the excessive damage flag for the zone is set at step 254. Referring again to FIG. 9, the excessive damage flag status is evaluated by the pressure management control routine 96 at decision step 256. If the excess damage flag is set, then pressure management control routine 96 returns to step 134 where the support zone target pressure is recalculated and the control routine 96 adjusts to the new target pressure and continues to monitor the operation of the air system controller 26. As discussed above, the target pressure calculated is dependent upon whether the damage flag has is set.

Figure 16:
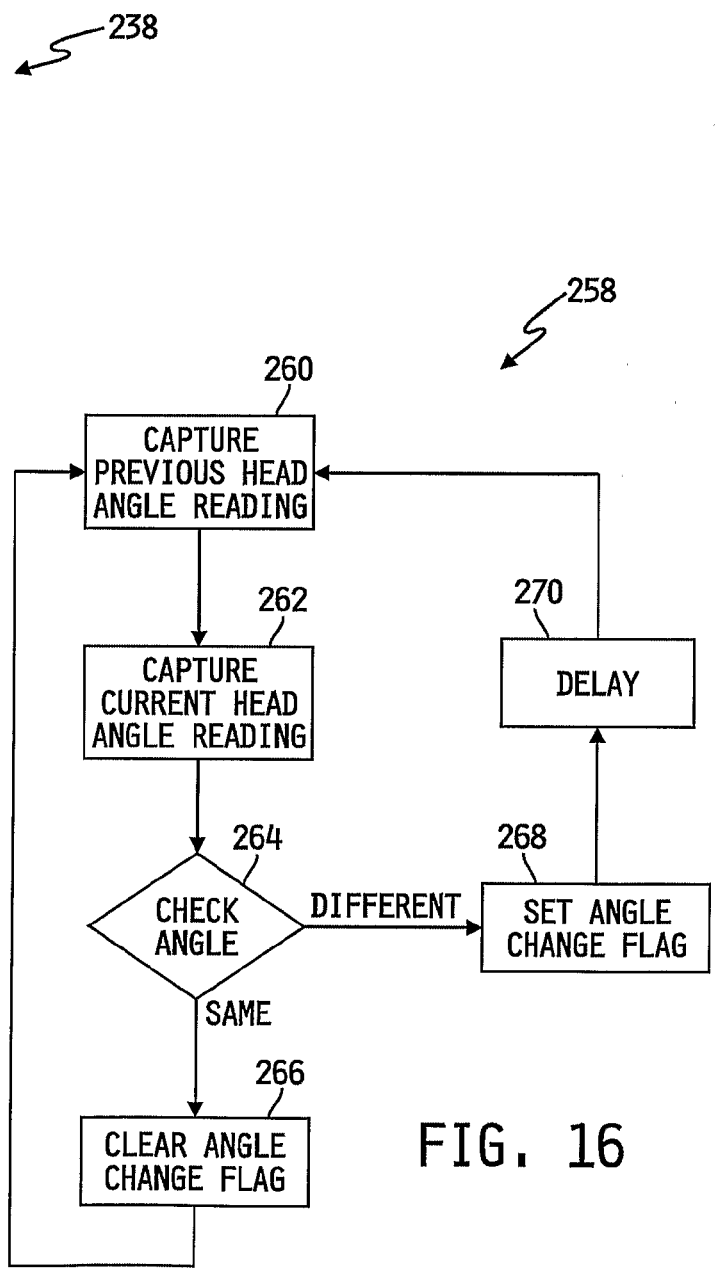
FIG. 16 is a flow chart of a subroutine which monitors for variations in an angle of articulation of a head portion of the hospital bed of FIG. 1.

If the excessive damage flag is not set, control routine 96 continues to a head angle monitor subroutine 258. Subroutine 258, shown in FIG. 16, captures the previous head angle reading from memory at step 260. At step 262, subroutine captures the current head angle reading. At step 264, the previous head angle reading and the current head angle reading are compared to determine if a change in head angle has been made. This determination may involve a tolerance band of change in the head angle to account for instability in the head angle reading from patient movement or other oscillations or system movement. In some embodiments, the head angle change determination may be supplemented by monitoring current to the head portion drive motor. In other embodiments, the head angle change determination may be supplemented by monitoring of inputs used to control the head angle to evaluate if a request to change head angle has been made.

If the determination is made that the current head angle is the same as the previous head angle, subroutine 258 advances to step 266 where the head angle change flag is cleared. The subroutine then loops back to step 260 to repeat the evaluation. If the head angle is determined to be different at step 264, the subroutine advances to step 268 where the head angle change flag is set. The subroutine 258 then advances to step 270 where a delay is built into the system to allow sufficient time for the change angle flag to be read by the control routine 96. In the illustrative embodiment, subroutine 258 is called once every 200 ms and the delay at step 270 is set at 200 ms so that if the flag is set, it will be read in at least one subsequent call. Once the delay is met, the subroutine 258 returns to step 260 to repeat the evaluation.

Referring again to FIG. 9, the pressure management operation control routine 96 advances from subroutine 258 to step 272 where the control routine 96 evaluates the status of the angle change flag. If the flag is set, control routine 96 returns to step 130 to recalculate the target pressure and continue through control routine 96. If the angle change flag is not set, control routine 96 returns to step 136 where the status of pressure in the zone is reevaluated and pressure management control routine 96 continues to control operation of the air system controller 26.

Additional details of a system in accordance with this disclosure are described in the appendices of U.S. Provisional Patent Application 60/702,645, which is incorporated by reference herein, where Appendix 1 describes a detailed hardware design, Appendix 2 describes a detailed software design, and Appendix 3 illustrates code used to execute the detailed software design. These Appendices are part of this disclosure and the details therein are considered to be a part of this patent application. It should be understood that the concepts disclosed herein are broadly applicable to person support systems which include inflatable supports such as bladders. As such, the details of the illustrative embodiment are applicable to that embodiment. When applied in other applications, the specific coefficients may vary from those disclosed herein and still be within the scope of this disclosure.

Although certain illustrative embodiments have been described in detail above, variations and modifications exist within the scope and spirit of this disclosure as described and as defined in the following claims.

The invention claimed is:

1. A patient support comprising:
   a source of pressurized air;
   a first bladder;
   a valve in fluid communication with the source of pressurized air and with the first bladder and configured to control the flow of air between the source of pressurized air and the first bladder;
   a first pressure sensor in direct contact with the air in the first bladder and producing a first pressure signal corresponding to the air pressure within the first bladder; and
   a controller in electrical communication with the source of pressurized air, the valve, and the first pressure sensor, the controller comprising (i) a processor, and (ii) a memory device electrically coupled to the processor, the memory device having stored therein a plurality of instructions which, when executed by the processor, cause the processor to:
   operate the source of pressurized air and the valve to inflate the first bladder,
   monitor the first pressure signal during the inflation to determine a time rate of change of pressure in the first bladder, and
   determine whether the patient is supported on the first bladder based on the time rate of change of pressure in the first bladder.

2. The patient support of claim 1, wherein the processor determines the rate of change of pressure in the first bladder by comparing the change from a first pressure to a second pressure over a known time interval and determines whether the patient is supported on the first bladder by determining if the rate of change of pressure is greater than a threshold value.

3. The patient support of claim 2, wherein the patient support further comprises a weight sensor in electrical communication with the processor to input a signal to the processor indicative of at least a portion of the weight of the patient supported on the patient support and the threshold value is a function of the patient weight.

4. The patient support of claim 3, wherein the patient support further comprises a position sensor in electrical communication with the processor to input a signal to the processor indicative of the articulation position of a head section of the patient support and the threshold value is a function of the articulation position.

5. The patient support of claim 4, wherein the processor filters the pressure signal during the inflation.

6. The patient support of claim 5, wherein the processor filters a pressure signal by taking an average of a number of pressure data points.

7. The patient support of claim 1, wherein the processor determines the rate of change of pressure in the first bladder by comparing the change from a first pressure to a second pressure over a known time interval and determines whether the patient is supported on the first bladder by determining if the rate of change of pressure is less than a threshold value.

8. The patient support of claim 7, wherein the patient support further comprises a weight sensor in electrical communication with the processor to input a signal to the processor indicative of at least a portion of the weight of the patient supported on the patient support and the threshold value is a function of the patient weight.

9. The patient support of claim 8, wherein the patient support further comprises a position sensor in electrical communication with the processor to input a signal to the processor indicative of the articulation position of a head section of the patient support and the threshold value is a function of the articulation position.

10. The patient support of claim 9, wherein the processor filters the pressure signal during the inflation.

11. The patient support of claim 9, wherein the processor filters a pressure signal by taking an average of a number of pressure data points.

12. A patient support comprising:
    a source of pressurized air;
    a first bladder;
    a first valve in fluid communication with the source of pressurized air and with the first bladder and configured to control the flow of air between the source of pressurized air and the first bladder;
    a first pressure sensor in direct contact with the air in the first bladder and producing a first pressure signal corresponding to the air pressure within the first bladder; and
    a controller in electrical communication with the source of pressurized air, valve, and first pressure sensor, the controller comprising (i) a processor, and (ii) a memory device electrically coupled to the processor, the memory device having stored therein a plurality of instructions which, when executed by the processor, cause the processor to:
    establish a target pressure for the first bladder,
    inflate the first bladder to a pressure within an acceptable tolerance of the target pressure,
    monitor the first pressure signal,
    compare the first pressure signal to the target pressure to determine a magnitude of deviation of the first pressure signal from the target pressure,
    accumulate the magnitude of pressure deviation over time, and
    output a signal if the accumulated magnitude exceeds a maximum value.

13. The patient support of claim 12, wherein the deviations when the first pressure signal is greater than the target value are weighted differently from deviations when the first pressure signal is less than the target value.

14. The patient support of claim 12, wherein the patient support further includes a second valve in fluid communication with the first bladder and configured to vent air out of the first bladder and wherein the output signal is utilized by the controller to cause the source of pressurized air and the first valve to inflate the first bladder to a pressure greater than the target pressure and to cause the second valve to deflate the first bladder back to a pressure within an acceptable tolerance of the first target pressure.

15. The patient support of claim 12, wherein the patient support further includes a second valve in fluid communication with the first bladder and configured to vent air out of the first bladder and wherein the output signal is utilized by the controller to cause the second valve to deflate the first bladder to a pressure below the target pressure and to cause the source of pressurized air and the first valve to inflate the first bladder to a pressure within an acceptable tolerance of the first target pressure.

16. A patient support comprising:
a source of pressurized air;
a first bladder;
a valve in fluid communication with the source of pressurized air and with the first bladder and configured to control the flow of air between the source of pressurized air and the first bladder;
a first pressure sensor in fluid communication with the first bladder and producing a first pressure signal indicative of air pressure within the first bladder; and
a controller in electrical communication with the source of pressurized air, valve, and first pressure sensor, the controller comprising (i) a processor, and (ii) a memory device electrically coupled to the processor, the memory device having stored therein a plurality of instructions which, when executed by the processor, cause the processor to:

determine a position of the patient supported on the first bladder,
monitor the first pressure signal to determine a time rate of change of pressure in the first bladder, and
determine whether the patient has changed positions on the first bladder based on a change in the time rate of change of the pressure in the first bladder.

17. The patient support of claim 16, wherein the processor determines the rate of change of pressure in the first bladder by comparing the change from a first pressure to a second pressure over a known time interval and determines whether the patient has changed positions by determining if the rate of change of pressure is greater than a threshold value.

18. The patient support of claim 17, wherein the patient support further comprises a weight sensor in electrical communication with the processor to input a signal to the processor indicative of at least a portion of the weight of the patient supported on the patient support and the threshold value is a function of the patient weight.

19. The patient support of claim 18, wherein the patient support further comprises a position sensor in electrical communication with the processor to input a signal to the processor indicative of the articulation position of a head section of the patient support and the threshold value is a function of the articulation position.

20. The patient support of claim 19, wherein the processor filters the pressure signal.

* * * * *